United States Patent
Kuwayama et al.

(10) Patent No.: US 8,464,591 B2
(45) Date of Patent: Jun. 18, 2013

(54) METHOD AND APPARATUS FOR JUDGING FRACTURE OF METAL STAMPED PRODUCT, PROGRAM AND COMPUTER-READABLE RECORDING MEDIUM

(75) Inventors: Takuya Kuwayama, Tokyo (JP); Atsushi Seto, Tokyo (JP); Noriyuki Suzuki, Tokyo (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 120 days.

(21) Appl. No.: 12/998,291

(22) PCT Filed: Oct. 6, 2009

(86) PCT No.: PCT/JP2009/067416
§ 371 (c)(1),
(2), (4) Date: Apr. 5, 2011

(87) PCT Pub. No.: WO2010/041662
PCT Pub. Date: Apr. 15, 2010

(65) Prior Publication Data
US 2011/0192232 A1    Aug. 11, 2011

(30) Foreign Application Priority Data
Oct. 7, 2008   (JP) .................................. 2008-260990

(51) Int. Cl.
*G01N 19/08*    (2006.01)
(52) U.S. Cl.
USPC ......................................................... 73/799
(58) Field of Classification Search
USPC ......................................................... 73/799
See application file for complete search history.

(56) References Cited

U.S. PATENT DOCUMENTS 4,225,553 A * 9/1980 Hirota et al. ................... 264/292
4,365,498 A * 12/1982 Hirota et al. ..................... 72/351

(Continued)

FOREIGN PATENT DOCUMENTS

JP    2-34225    2/1990
JP    4-75800    3/1992

(Continued)

OTHER PUBLICATIONS

International Search Report dated Nov. 10, 2009 issued in corresponding PCT Application No. PCT/JP2009/067416.

(Continued)

*Primary Examiner* — Lisa Caputo
*Assistant Examiner* — Jonathan Dunlap
(74) *Attorney, Agent, or Firm* — Kenyon & Kenyon LLP

(57) ABSTRACT

In the process of target stamping for fracture judgment, an acquisition unit acquires, as target data for fracture judgment, strain of a target die to be measured over the duration from the start time of stamping measured by strain measuring units to the finishing time of stamping, and also acquires production conditions typically by measurement. An extraction unit extracts the reference data, which gives the minimum total of differences between the production conditions of the reference data and the production conditions of the target data for fracture judgment, as the comparative data. A judging unit compares strain in the comparative data extracted by the extraction unit and strain in the target data for fracture judgment, and judges occurrence of a crack in a stamped product, if the maximum value of the difference is not smaller than a predetermined value.

13 Claims, 5 Drawing Sheets

U.S. PATENT DOCUMENTS

| | | | |
|---|---|---|---|
| 5,448,902 A * | 9/1995 | Thoms et al. | 72/31.13 |
| 5,507,189 A * | 4/1996 | Kim et al. | 73/838 |
| 5,600,991 A * | 2/1997 | Munzen | 72/348 |
| 6,456,898 B1 * | 9/2002 | Modesto et al. | 700/206 |
| 8,234,897 B2 * | 8/2012 | Kuwayama et al. | 72/21.4 |
| 2007/0240470 A1 | 10/2007 | Suzuki et al. | |
| 2008/0092620 A1 | 4/2008 | Suzuki et al. | |
| 2009/0120151 A1 | 5/2009 | Kuwayama et al. | |

FOREIGN PATENT DOCUMENTS

| | | |
|---|---|---|
| JP | 05-337554 | 12/1993 |
| JP | 09-029358 | 2/1997 |
| JP | 2004-249365 | 9/2004 |
| JP | 2005-161399 | 6/2005 |
| JP | 2005-199336 | 7/2005 |
| JP | 2005-254300 | 9/2005 |
| JP | 2006-75884 | 3/2006 |
| JP | 2006-136926 | 6/2006 |
| WO | WO 2007/080983 | 7/2007 |

OTHER PUBLICATIONS

Kuwayama et al. "Development of Total Forming Technologies for High Strength Steel Sheet—Development of Tool Friction Sensor-", Proceedings of Annual Congress of JSAE, No. 19-07, pp. 17-20 (2007).

International Preliminary Report on Patentability dated May 26, 2011, issued in corresponding PCT Application No. PCT/JP2009/067416.

* cited by examiner

FIG. 1
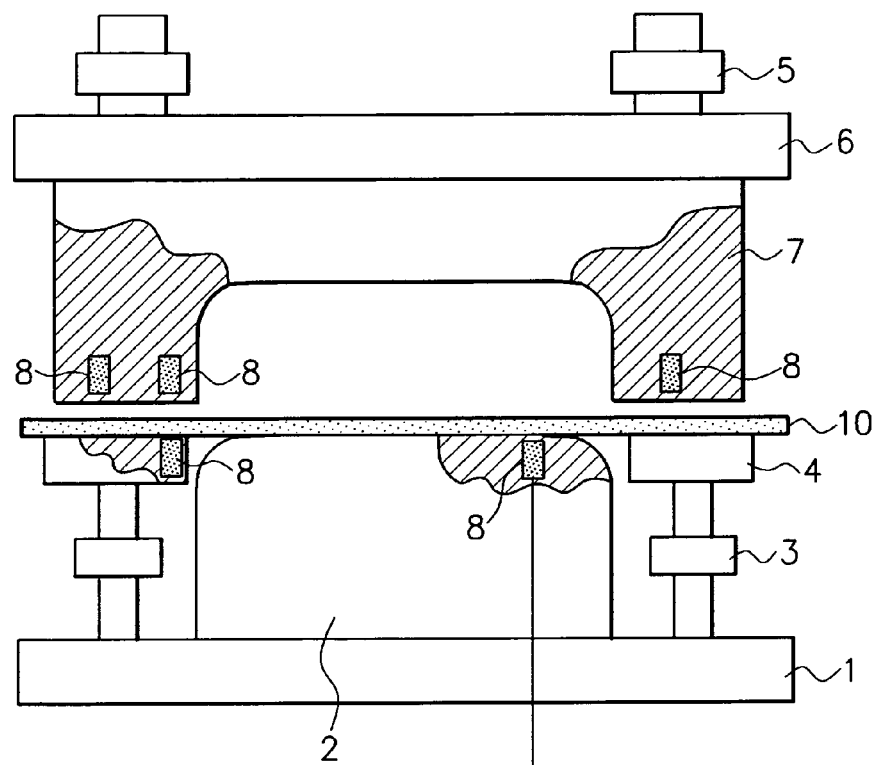
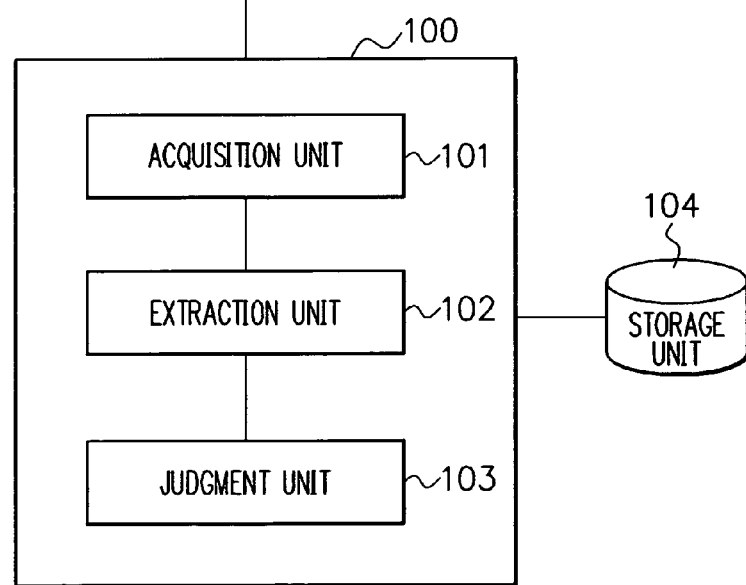

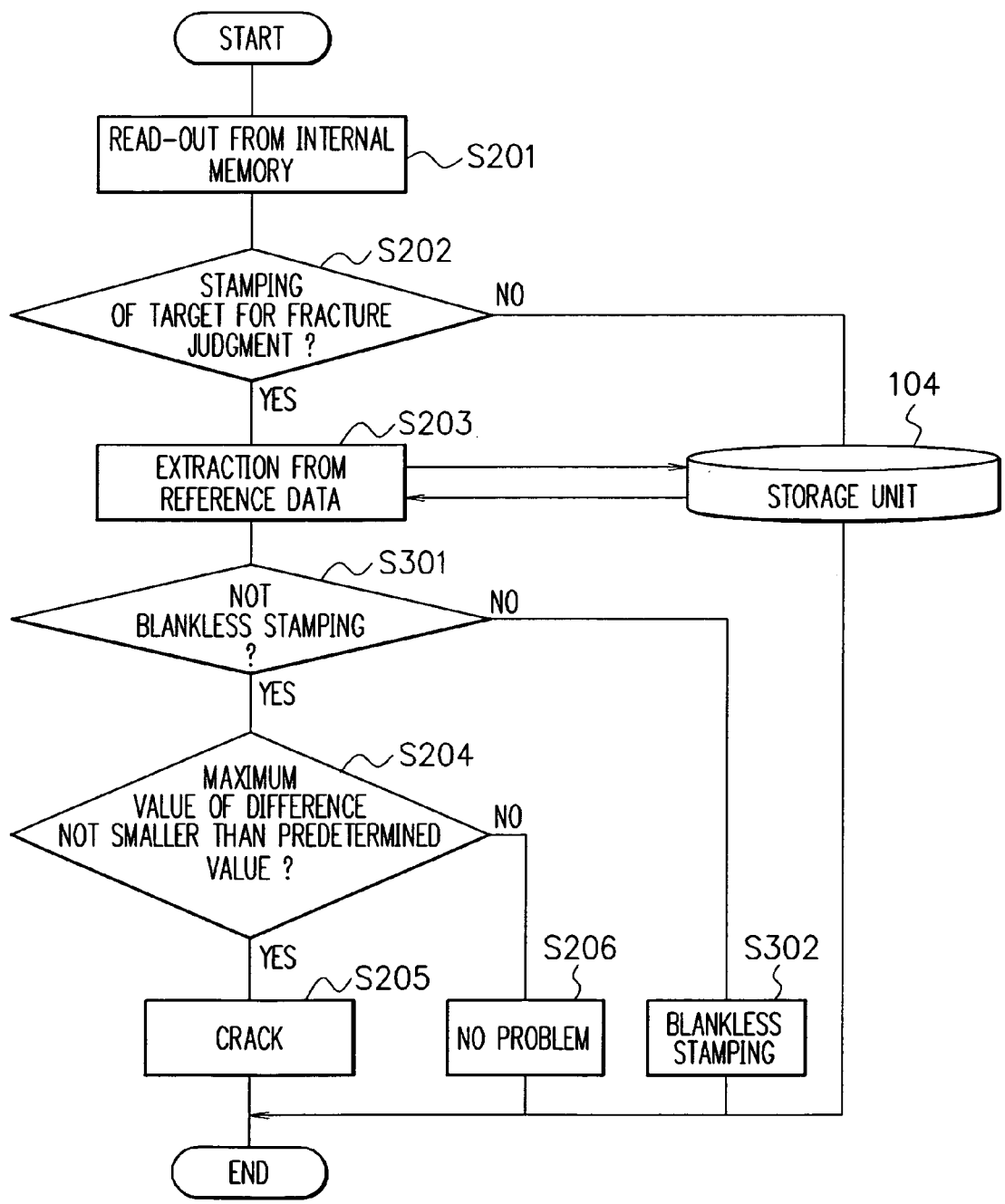
F I G. 4

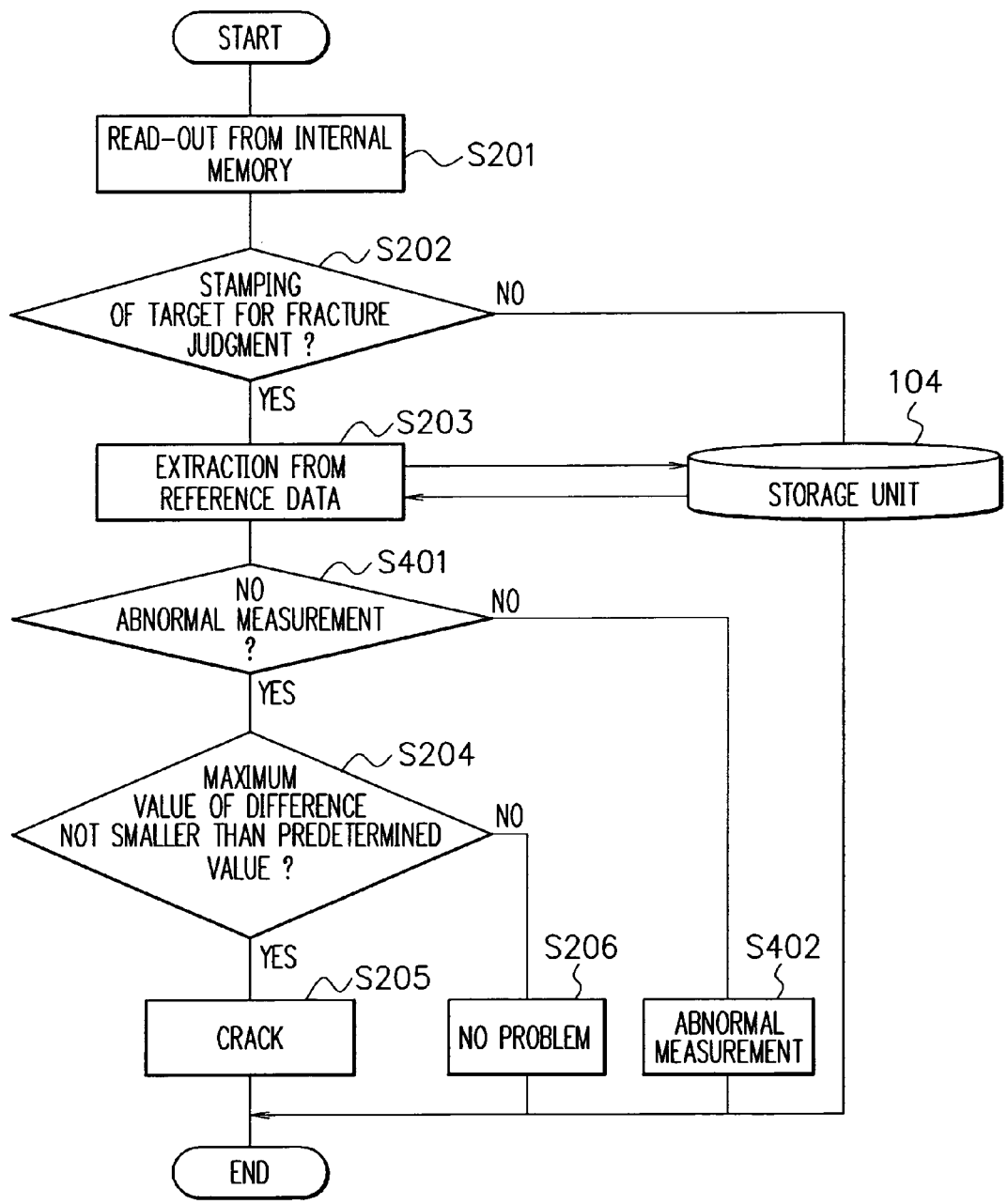

METHOD AND APPARATUS FOR JUDGING FRACTURE OF METAL STAMPED PRODUCT, PROGRAM AND COMPUTER-READABLE RECORDING MEDIUM

This application is a national stage application of International Application No. PCT/JP2009/067416, filed 6 Oct. 2009, which claims priority to Japanese Application No. 2008-260990, filed 7 Oct. 2008, which is incorporated by reference in its entirety.

TECHNICAL FIELD

The present invention relates to a method of judging fracture in metal stamped products, an apparatus, a program, and a computer-readable recording medium, and in particular to techniques preferably adoptable to detection of crack in the process of stamping of various metal materials of iron base, non-iron base and stacked materials.

BACKGROUND ART

In the process of stamping, in particular dies are applied with pressurizing force of a stamping press, reaction force due to deformation resistance of work and so forth, and cause elastic deformation. The elastic deformation of the dies is referred to as die strain. Since any stamping failure such as fracture in the process of stamping may vary the amount of die strain to be produced, so that it is very important to measure the amount of die strain. The die strain may, however, vary depending not only on the stamping failure, but also on external disturbance factors such as variation in material strength of works, changes in temperature and so forth. It is, therefore, expected to develop a technique of more effectively predicting stamping failure phenomena based on information of the amount of die strain.

As a device for measuring die strain, Patent Document 1 discloses a boat-form correction device for a press brake which bends a workpiece between a punch attached to an upper beam and a die attached to a lower beam, moved to join with and disjoin from each other. The boat-form correction device has a plurality of upper beam strain sensors for detecting deflection of the upper beam provided in the longitudinal direction of the upper beam; a plurality of lower beam strain sensors for detecting deflection of the lower beam provided in the longitudinal direction of the lower beam; a plurality of actuators disposed between the lower beam and a lower die, or between the upper beam and an upper die, in a distributed manner in the direction of line of bending so as to apply pressurizing force to the lower die or the upper die; and a control unit which interrupts descending of the upper beam at a point of time between the start and end of pressurizing, fetches outputs of detection by the upper beam strain sensors and the lower beam strain sensors during the interruption, calculates the amount of deflection of the upper beam and the lower beam based on the outputs of detection, controls operations of the plurality of actuators based on the calculated results so as to adjust the amount of deflection of the upper beam and lower beam to appropriate values, and then restarts control of the pressurizing.

As a device having a model for predicting deformation of dies, Patent Document 2 discloses a stamping die which has a load detection unit 4; a stroke detection unit 5; a detection unit 6 for the number of times of stamping; a detection unit 7 for die temperature; a deformation prediction model which is composed of any one of, or a plurality of models selected from a wear model 9 of die, thermal deformation model 10 of die, load-deformation model 11 of die, thermal deformation model 12 of work, and a spring back model 13 of work; a multi-variable control signal generator 14; and an actuator 15 such as a piezoelectric element, for deforming the inner wall of a cavity 3, aiming at providing a stamping dies capable of precisely and automatically controlling dimension and geometry of products, for the purpose of simplifying the process by promoting production of near-net-shape stamped products in stamping. Note that the reference numerals attached herein are those used in Patent Document 2.

As a device for measuring strain of dies, Patent Document 3 discloses an invention configured as described below, aiming at providing dies capable of detecting angle of bending of works and strain of works, and a strain sensor unit used therefor. In a strain-producible region where strain of a work W occurs in the process of working, and in a plane normal to a work-supporting surface 3U on which a main unit 3 of die supports the work, the main unit 3 of die is provided with strain sensors 9 buried therein at two or more positions close to, and distant from, the position of working of the work W. The plurality of strain sensors 9 are disposed in a traversing manner between the top surface 3U of a main unit of die 3 and groove-forming surface 5F having a bend groove 5 formed therein. A strain sensor unit has the sensors for detecting strain at a plurality of positions on the base 13 composed of an insulating material. The base 13 is configured to have sensor-attachment surfaces 21A, 21B having the sensors 9 attached thereto, and bonding surfaces allowing thereon the base 13 to be bonded to the inner surface of a fitting hole in an integrated manner, so as to form a gap between each sensor attachment surface and the inner surface of the fitting hole, when the base is fitted to the fitting hole. The reference numerals attached herein are those used in Patent Document 3.

As a device for measuring strain of dies, Patent Document 4 discloses an invention configured as described below, aiming at providing dies capable of increasing pressurizing force depending on the depth (stroke) of works in a V-shape groove. A die 1, used for bending a sheet-form work W into V-shape, has an inclined surface 5 composing a V-groove 3, formed into convex curved surfaces 5U, 5L, wherein a curvature DR2 of the lower portion of the curved surface is larger than a curvature DR1 of the upper portion of the curved surface, so as to allow the curved surfaces 5U, 5L to contact with a work W in a mode of rolling contact in the process of bending. The die 1, used for bending a sheet-form work W into V-shape, is alternatively configured to have an inclined surface 5 for forming a V-groove 3, formed into a convex curved surface which is in contact with an oval. The die 1 has a sensor 7 for detecting deformation, at a position close to the inclined surface 5. The reference numerals attached herein are those used in Patent Document 4.

As a device for measuring strain of dies, Patent Document 5 discloses an invention configured as described below, aiming at providing a method and a device for detecting angle of bending of works by detecting strain of dies. In the process of bending of a sheet-form work W, a deformation pattern of a die 5 is measured using strain sensors S1 to S4 provided to the die 5, a predictive equation is determined by comparing the measured strain pattern with a plurality of strain patterns preliminarily stored in a database 15, friction coefficient is found from the thus-determined pattern predictive equation, and an angle of bending of the work is calculated based on the value detected by the strain sensors, using the pattern predictive equation. The strain sensors for detecting strain of die in the process of bending of a work are provided at a plurality of positions. A control unit 9 has a database 15, a predictive equation determining unit 17 which determines a pattern predictive equation by comparing detected strain of the die 5 with strain patterns stored in the database 15, and a calculation unit 21 which determines friction coefficient using the pattern predictive equation. The reference numerals attached herein are those used in Patent Document 5.

As a device for measuring strain of dies, Patent Document 6 describes an invention configured as described below, aiming at ensuring desirable stamping. An arithmetic unit 104 for conditional setting compares actual values of material characteristics sent from a material characteristic data providing unit 101 through a network 105 with standard values, and corrects conditions of forming such as sliding speed and blank holding force depending on results of the comparison. A control unit 300 controls a stamping press 102 so as to start stamping of a work 300 according to the corrected conditions of forming. In this way, cracks and wrinkles are prevented as possible from generating in the process of stamping of a work 300, so as to obtain acceptable products having a geometry identical as possible. The reference numerals attached herein are those used in Patent Document 6.

Patent Document 7 discloses a stamping press for thin sheet, having a punch, a die, a blank holding die, a frictional force measurement unit attached between the die and the blank holding die, and a blank holding force adjustment unit. Frictional force is directly measured by the frictional force measurement unit, and blank holding force is further controlled by a blank holding force adjustment unit so as to adjust the frictional force to a predetermined value. The invention aims at applying an appropriate frictional force irrespective of variable factors such as lubricating performance between the die and a work, surface property and so forth, and thereby constantly providing acceptable products.

Patent Document 8 discloses an invention configured as described below, aiming at providing a stamping press capable of controlling die strain in the process of stamping. The invention includes a punch; a die which moves relative to the punch; a strain measuring unit provided inside a target to be controlled which is at least either one of the punch and the die, so as to measure the amount of strain of the target to be controlled produced as the stamping proceeds; and a strain control unit provided to the target to be controlled so as to control the amount of strain produced as the stamping proceeds. The strain control unit controls the amount of drive of the target to be controlled so as to adjust the amount of strain measured by the strain measuring unit within a predetermined range in the process of forming.

The present inventors disclosed a stamping press in Non-Patent Document 1, which has a built-in piezoelectric element (die friction sensor) for measuring compressive and tensile strain in the orthogonal directions, provided in the vicinity of a shoulder portion of a die, and made clear that the geometry of the works, such as spring-back and tilting, may be predictable from information given by the die friction sensor.

CITATION LIST

Patent Literature

Patent Document 1: Japanese Laid-Open Patent Publication No. H5-337554
Patent Document 2: Japanese Laid-Open Patent Publication No. H9-029358
Patent Document 3: Japanese Laid-Open Patent Publication No. 2005-199336
Patent Document 4: Japanese Laid-Open Patent Publication No. 2005-254300
Patent Document 5: Japanese Laid-Open Patent Publication No. 2006-136926
Patent Document 6: Japanese Laid-Open Patent Publication No. 2006-075884
Patent Document 7: Japanese Laid-Open Patent Publication No. 2004-249365
Patent Document 8: International Publication Pamphlet No. WO 07/080,983

Non-Patent Literature

Non-Patent Document 1: Proceedings of Annual Congress of JSAE, No. 19-07, pp. 17-20 (2007)

SUMMARY OF THE INVENTION

Technical Problem

Patent Document 1 discloses the invention regarding a device having a function of measuring strain of dies, but gives no description on detection of troubles such as cracks in the process of stamping.

The invention of Patent Document 1 discloses nothing but that the beam strain sensors are provided in the longitudinal direction of the beams of the press brake. For the purpose of precisely measuring strain of dies in stamping using dies having more complex geometries than those used in the press brake, it may be necessary to provide functions of measuring strain inside the dies such as the punch, die and blank holding die, and to directly measure strain of dies as produced. The invention disclosed in Patent Document 1 is not sufficient for this purpose.

According to the invention disclosed in Patent Document 1, the forming is once interrupted before completion, the amount of strain of the upper and lower beams are detected and then optimized by the actuators during the interruption, and the forming is restarted. However, in stamping, frictional force between the work and the tools measured during interruption of stamping may largely be different from that measured during the interruption, unlike the forming mainly characterized by bending using the press brake. For this reason, the invention disclosed in Patent Document 1 may give only the amount of deformation of die different from that measured in the process of stamping with an insufficient level of accuracy of measurement, even if the invention is applied to stamping.

In conclusion, the invention disclosed in Patent Document 1 is insufficient for detecting cracks in the process of stamping.

Patent Document 2 discloses the invention regarding a device having a model for predicting deformation of dies, but gives no description on detection of failures such as cracks in the process of stamping.

The invention disclosed in Patent Document 2 includes a load detection unit for detecting load applied over the entire body of the dies, and a load-deformation model of dies, which are used for detecting deformation of dies. However, the amount of change in the load possibly applied to the entire body of the dies when a crack locally occurred in a stamped product is very small, and is difficult to detect. Even if the detection were successful, it is impossible to determine a point of occurrence of such micro-crack causative of the amount of change.

In conclusion, the invention disclosed in Patent Document 2 is insufficient for detecting cracks in the process of stamping.

Patent Document 3 discloses the invention regarding the device for measuring strain of dies, but gives no description on detection of cracks in stamped components in the process of stamping.

According to the invention disclosed in Patent Document 3, a strain sensor is buried in a plane normal to a work-supporting surface on which a work is supported on the main unit of die. The main unit of die 3 used for bending works may be provided with the buried strain sensor according to the invention disclosed in Patent Document 3, since the upper surface 3U which corresponds to a work-supporting surface is given flat, and thereby the surface normal to the upper surface 3U and the longitudinal direction of the bend groove 5 may be unconditionally given. However, in stamping possibly suffering from problems of cracks, dies for stamping generally have geometries more complicated than those of dies for bending. The work-supporting surface of the dies for stamping have a complex curved profile, rather than a flat profile, so that it is impossible to define a normal to the surface. Even the direction such as defined for the bend groove 5 cannot be defined. It is, therefore, impossible to provide the buried strain sensor to the dies for stamping, according to the invention disclosed in Patent Document 3.

In conclusion, the invention disclosed in Patent Document 3 is insufficient for detecting cracks in the process of stamping.

Patent Document 4 discloses the invention regarding the device for measuring strain of dies, but gives no description on detection of cracks in stamped components in the process of stamping.

Patent Document 4 also gives no specific description on a sensor for detecting strain, only giving a description on that the configuration described in Non-Patent Document, using the buried strain sensor, is preferable. Non-Patent Document mentioned herein, however, relates to bending, so that it is impossible to provide a buried strain sensor to dies for stamping according to the invention disclosed in Patent Document 4.

In conclusion, the invention disclosed in Patent Document 4 is insufficient for detecting cracks in the process of stamping.

Patent Document 5 discloses the invention regarding the device of measuring strain of dies, but gives no description on detection of cracks in stamped products in the process of stamping.

Similarly to the above-described Patent Document 3 and Patent Document 4, there is no specific description in the text on the strain sensor except that it has the same configuration with that described in Non-Patent Document, and Non-Patent Document mentioned herein relates only to bending. For this reason, it is impossible to provide a buried strain sensor to dies for stamping, according to the method disclosed in Patent Document 5.

In conclusion, the invention disclosed in Patent Document 5 is insufficient for detecting cracks in the process of stamping.

Patent Document 6 discloses the invention regarding the device of measuring strain of dies, but gives no description on detection of cracks in stamped products in the process of stamping.

The strain sensor appears in FIG. 3, but is not specifically described in the text. For this reason, it is impossible to provide a buried strain sensor according to the method disclosed in Patent Document 6.

In conclusion, the invention disclosed in Patent Document 6 is insufficient for detecting cracks in the process of stamping.

Patent Document 7 aims at measuring frictional force by placing some structure on the blank holding die or on the dies, but not at directly measuring strain of the blank holding die or the dies. For detection of cracks in the process of stamping, it is indispensable to directly measure strain of the dies such as punch, die, and blank holding die. The invention disclosed in Patent Document 7 is therefore insufficient for this purpose.

Patent Document 8 discloses the invention regarding the device for measuring strain of dies, but gives no description on detection of cracks in stamped components in the process of stamping. The invention disclosed in Patent Document 8 is therefore insufficient for detection of cracks in the process of stamping.

The invention disclosed in Non-Patent Document 1 described that the built-in friction sensors buried in the vicinity of the die shoulder can also detect cracks in stamped products, but gives no specific description on procedures and how to judge fracture in stamped products using the strain sensor. Accordingly, actual judgment of whether cracks really exist or not inevitably relies upon trial-and-error.

The present invention is conceived after considering the above-described problems, and an object thereof is to provide a method and an apparatus for judging fracture of metal stamped products, a program and a computer-readable recording medium, and in particular to provide techniques preferably adoptable to detection of cracks in stamping of various metal materials such as those of iron-base, non-iron-base and stacked materials.

Solution to Problem

Means for solving the above-described problems proposed by the present invention are as follow.

(1)

A method of judging fracture in a metal stamped product which judges a crack in a metal stamped product formed using a punch and a die, using a strain measuring unit which measures strain of at least either of the punch and the die selected as a target die to be measured, and a storage unit which stores, as reference data, strain of the target die to be measured over the entire period or a partial period from the start time of stamping to the finishing time of stamping, and production conditions including at least sliding speed, with respect to a plurality of stamped product having no crack produced therein, the method includes:

an acquisition step which acquires, in a target stamping for fracture judgment, and as target data for fracture judgment, strain of the target die to be measured by the strain measuring unit over the entire period or a partial period from the start time of stamping to the finishing time of stamping, and acquires production conditions including at least sliding speed;

an extraction step which extracts, from the reference data, the one satisfying a predetermined condition as comparative data, based on the production conditions of the reference data extracted from the storage unit, and also based on the production conditions of the target data for fracture judgment, and a judgment step which compares strain in the comparative data and strain in the target data for fracture judgment, and judges occurrence of a crack in a stamped product, if a predetermined condition is satisfied.

(2)

The method of judging fracture in a metal stamped product according to (1), wherein the production conditions further includes, in addition to the sliding speed, at least one of production time, ambient temperature, humidity, blank holding force, lot number of work, blank process position information traceable from material lot, tensile strength of work, yield strength of work, amount of uniform elongation of work, and thickness of work.

(3)

The method of judging fracture in a metal stamped product according to (1), wherein, the extraction step extracts the reference data, which gives the minimum total of differences between the production conditions of the reference data extracted from the storage unit and the production conditions of the target data for fracture judgment, as the comparative data.

(4)

The method of judging fracture in a metal stamped product according to (1), wherein the judgment step judges occurrence of a crack in a stamped product, if a maximum value of difference between strain of the comparative data and strain of the target data for fracture judgment exceeds a predetermined value.

(5)

The method of judging fracture in a metal stamped product according to any one of (1) to (4), wherein, further by using a blank holding die, at least one of the punch, the die and the blank holding die is selected as the target die to be measured.

(6)

The method of judging fracture in a metal stamped product according to (1), wherein the extraction step extracts the reference data based on production conditions of the reference data extracted from the storage unit, and production conditions of the target data for fracture judgment, over the duration from the start time of stamping up to the time when the stamping proceeds beyond a predetermined range of the stroke of stamping, as the comparative data.

(7)

The method of judging fracture in a metal stamped product according to (3), wherein the extraction step extracts the reference data, which gives the minimum total of differences between the production conditions of the reference data extracted from the storage unit and the production conditions of the target data for fracture judgment, over the duration from the start time of stamping up to the time when the stamping proceeds by at least 30% or more of the stroke of stamping, as the comparative data.

(8)

The method of judging fracture in a metal stamped product according to (7), further comprising a step of comparing maximum values of strain of the comparative data over the duration from the start time of stamping up to the time when the stamping proceeds by at least 30% or more of the stroke of stamping, with a maximum value of strain of the target data for fracture judgment; assuming a maximum value of strain of the target data for fracture judgment as a result of blankless stamping if the value is smaller than 20% of a maximum value of strain of the comparative data, and excepting the value from the fracture judgment; and subjecting only a maximum value of strain of the target data for fracture judgment not smaller than 20% of the maximum value of strain of the comparative data, to the judgment step.

(9)

The method of judging fracture in a metal stamped product according to (7), further comprising a step of comparing strain waveforms of the comparative data over the duration from the start time of stamping up to the time when the stamping proceeds by at least 30% or more of the stroke of stamping, with a strain waveform of the target data for fracture judgment; assuming a strain waveform of the target data for fracture judgment as a result of abnormal measurement if the waveform shows a correlation coefficient with respect to the strain waveform of the comparative data of smaller than 0.6, and excepting the strain waveform from the fracture judgment; and subjecting only a strain waveform of the target data for fracture judgment showing a correlation coefficient with respect to the strain waveform of the comparative data of not smaller than 0.6, to the judgment step.

(10)

The method of judging fracture in a metal stamped product according to (3), wherein the extraction step extracts the reference data, which gives the minimum total of differences between the production conditions of the reference data extracted from the storage unit and the production conditions of the target data for fracture judgment, over the duration from the time when the stamping proceeds by at least 60% of the stroke of stamping from the start time of stamping, up to the time when a reverse operation of a slide of a stamping press, after reaching the bottom dead position of stamping and turning into the reverse operation, proceeds by at least 20% or more of the stroke of stamping from the bottom dead position, as the comparative data.

(11)

The method of judging fracture in a metal stamped product according to (10), further comprising a step of comparing strain waveforms of the comparative data over the duration from the time when the stamping proceeds by at least 60% of the stroke of stamping from the start time of stamping, up to the time when a reverse operation of a slide of a stamping press, after reaching the bottom dead position of stamping and turning into the reverse operation, proceeds by at least 20% or more of the stroke of stamping from the bottom dead position, with a strain waveform of the target data for fracture judgment; assuming a strain waveform of the target data for fracture judgment as a result of abnormal measurement if the waveform shows a correlation coefficient with respect to the strain waveform of the comparative data of smaller than 0.6, and excepting the strain waveform from the fracture judgment; and subjecting only a strain waveform of the target data for fracture judgment showing a correlation coefficient with respect to the strain waveform of the comparative data of not smaller than 0.6, to the judgment step, over the duration from the time when the stamping proceeds by at least 60% of the stroke of stamping from the start time of stamping, up to the time when a reverse operation of a slide of a stamping press, after reaching the bottom dead position of stamping and turning into the reverse operation, proceeds by at least 20% or more of a stroke of stamping from the bottom dead position.

(12)

A fracture judgment apparatus for judging fracture in a metal stamped product which judges a crack in a metal stamped product formed using a punch and a die, which include:

a strain measuring unit which measures strain of at least either of the punch and the die selected as a target die to be measured;

a storage unit which stores, as reference data, strain of the target die to be measured over the entire period or a partial period from the start time of stamping to the finishing time of stamping, and production conditions including at least sliding speed, with respect to a plurality of stamped product having no crack produced therein;

an acquisition unit which acquires, in a target stamping for fracture judgment, and as target data for fracture judgment, strain of the target die to be measured by the strain measuring unit over the entire period or a partial period from the start time of stamping to the finishing time of stamping, and acquires production conditions including at least sliding speed;

an extraction unit which extracts, from the reference data, the one satisfying a predetermined condition as comparative data, based on the production conditions of the reference data extracted from the storage unit, and also based on the production conditions of the target data for fracture judgment; and a judgment unit which compares strain in the comparative data and strain in the target data for fracture judgment, and judges occurrence of a crack in a stamped product, if a predetermined condition is satisfied.

(13)

A computer-readable recording medium storing a program which allows a computer to execute fracture judgment of a metal stamped product, which judges fracture in a metal stamped product formed using a punch and a die, using a strain measuring unit which measures strain of at least either of the punch and the die selected as a target die to be measured, and a storage unit which stores, as reference data, strain of the target die to be measured over the entire period or a partial period from the start time of stamping to the finishing time of stamping, and production conditions including at least sliding speed, with respect to a plurality of stamped product having no crack produced therein, the program includes:

an acquisition process which acquires, in a target stamping for fracture judgment, and as target data for fracture judgment, strain of the target die to be measured by the strain measuring unit over the entire period or a partial period from the start time of stamping to the finishing time of stamping, and acquires production conditions including at least sliding speed;

an extraction process which extracts, from the reference data, the one satisfying a predetermined condition as comparative data, based on the production conditions of the reference data extracted from the storage unit, and also based on the production conditions of the target data for fracture judgment; and a judgment process which compares strain in the comparative data and strain in the target data for fracture judgment, and judges occurrence of a crack in a stamped product, if a predetermined condition is satisfied.

(14)

A computer-readable recording medium storing program according to (13).

Advantageous Effects of Invention

According to this invention, cracks possibly produced in the process of stamping of various metal materials such as those of iron-base, non-iron-base and stacked products may precisely be judged.

BRIEF DESCRIPTION OF THE DRAWINGS

FIG. 1 is a drawing illustrating configurations of a stamping press and a fracture judgment apparatus.

FIG. 4 is a flow chart regarding judgment of fracture.

FIG. 5 is a flow chart regarding judgment of fracture.

DESCRIPTION OF EMBODIMENTS

Figure 2:
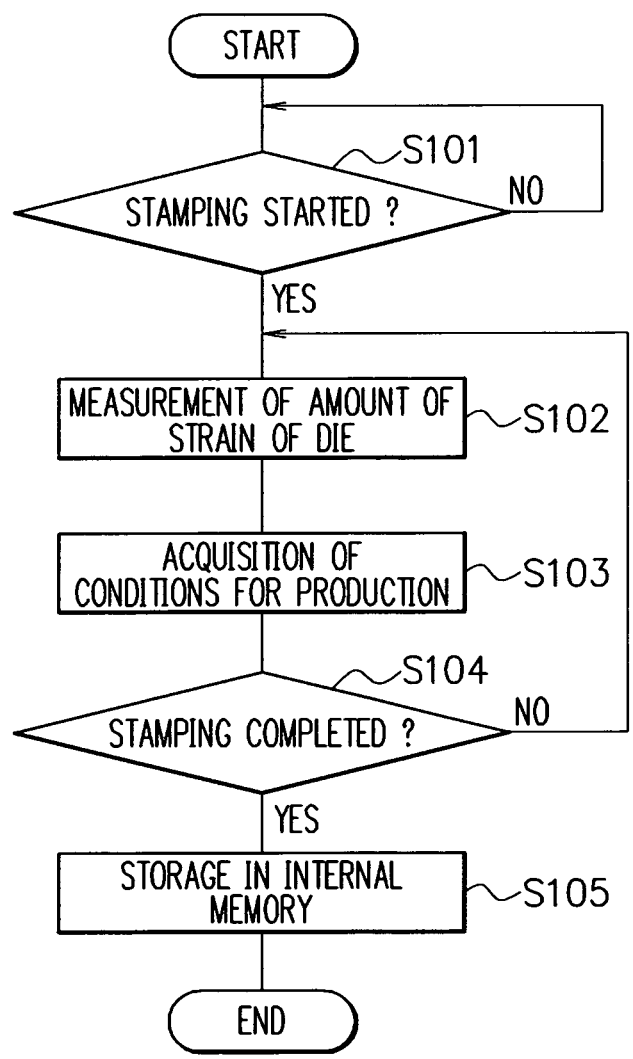
FIG. 2 is a flow chart regarding measurement of strain of a target die to be measured, and acquisition of production conditions.

Preferred embodiments of the present invention will be explained below, referring to the attached drawings.

First Embodiment

FIG. 1 illustrates configurations of a stamping press and a fracture judgment apparatus 100 of this embodiment. In the stamping press, a punch 2 is attached to a bolster 1 of the stamping press, a blank holding die 4 is attached to a blank holding load adjustment unit 3, and a die 7 is attached to an upper slide 6 which is driven by a stamping load/rate adjustment unit 5. A sheet 10 as a work is placed on the punch 2 and the blank holding die 4.

Assuming at least any one of punch 2, die 7 and blank holding die 4 as a target die to be measured, strain measuring units 8 measure strain produced therein. Each strain measuring unit 8 is configured by a strain gauge, a piezoelectric element, a FBG sensor using an optical fiber, and so forth. Although the strain measuring units 8 may be placed on the surface of the target die to be measured, they may preferably be placed inside the target die to be measured for precise measurement of strain, without limitation in the number of placement thereof. Although the stamping press illustrated in FIG. 1 has the blank holding die, at least either of the punch 2 and the die 7 may alternatively be assumed as the target die to be measured, if the blank holding die is not provided.

In the fracture judgment apparatus 100, the storage unit 104 is configured typically by a hard disk drive of a computer or the like, and stores, as reference data, and production conditions including at least sliding speed, with respect to a plurality of stamped product having no crack produced therein, over the entire period or a partial period from the start time of stamping to the finishing time of stamping, wherein the production conditions include production time, ambient temperature, humidity, sliding speed, blank holding force, lot number of work, blank process position information traceable from material lot, tensile strength of work, yield strength of work, amount of uniform elongation of work, and thickness of work. The storage unit 104 contains the reference data of stamped products preliminarily confirmed, by inspection by an inspector or by any publicly-known crack inspection technique, to have no cracks produced therein. In addition, the storage unit 104 may be configured to have the reference data of stamped products, which were proven to be "no problem" by the fracture judgment apparatus 100 of this embodiment, and sequentially accumulated therein as described later.

The acquisition unit 101 acquires, in a target stamping for fracture judgment, and as target data for fracture judgment, strain of the target die to be measured by the strain measuring unit 8 over the period from the start time of stamping to the finishing time of stamping, and acquires production conditions including at least sliding speed typically by measurement; wherein the production conditions include production time, ambient temperature, humidity, sliding speed, blank holding force, lot number of work, blank process position information traceable from material lot, tensile strength of work, yield strength of work, amount of uniform elongation of work, and thickness of work.

The extraction unit 102 extracts a reference data which satisfy a predetermined condition, as a comparative data, based on the production conditions of the reference data extracted from the storage unit 104, and also based on the production conditions of the target data for fracture judgment.

The judgment unit 103 compares strain in the comparative data extracted by the extraction unit 102 and strain in the target data for fracture judgment, and judges occurrence of a crack in a stamped product, if a predetermined condition is satisfied.

In the present invention, the storage unit stores the production conditions, which contain at least sliding speed, as the reference data. The acquisition step acquires production conditions which contain at least sliding speed. A reason why the sliding speed is essential as the production condition is that also the strain possibly produced in the target die to be measured varies in association with changes in the sliding speed.

One possible cause may be ascribable to effect of changes in impact load which generates when the die 7, as a heavy matter, collides against the punch and the blank holding die 4 in the vicinity of the bottom dead position, induced by changes in the sliding speed. Another possible cause may be effect of changes in water hammer effect, which generates in pressure piping of the blank holding load adjustment unit 3, induced by changes in the sliding speed. Still other possible causes include strain rate dependence of deformation resistance, sliding rate dependence of slide resistance, and so forth.

Another reason why the sliding speed is essential as the production condition is that accuracy of comparison of strain of the target data for fracture judgment with strain of the comparative data with respect to the target die to be measured, which takes place in the judgment step described later, may be improved.

Strain generated in the target die to be measured gives an output of characteristic waveform depending on stroke of stamping, that is, a relative positional relation between the upper die and the lower die. Measuring instruments for measuring the waveform are generally configured to perform data sampling at regular intervals of time. By using information of sliding speed, the strain data sampled at a regular intervals of time may now be converted into data corresponded to the stroke of stamping. In this way, the strain data may be compared in the judgment step in a simple and precise manner.

Figure 3:
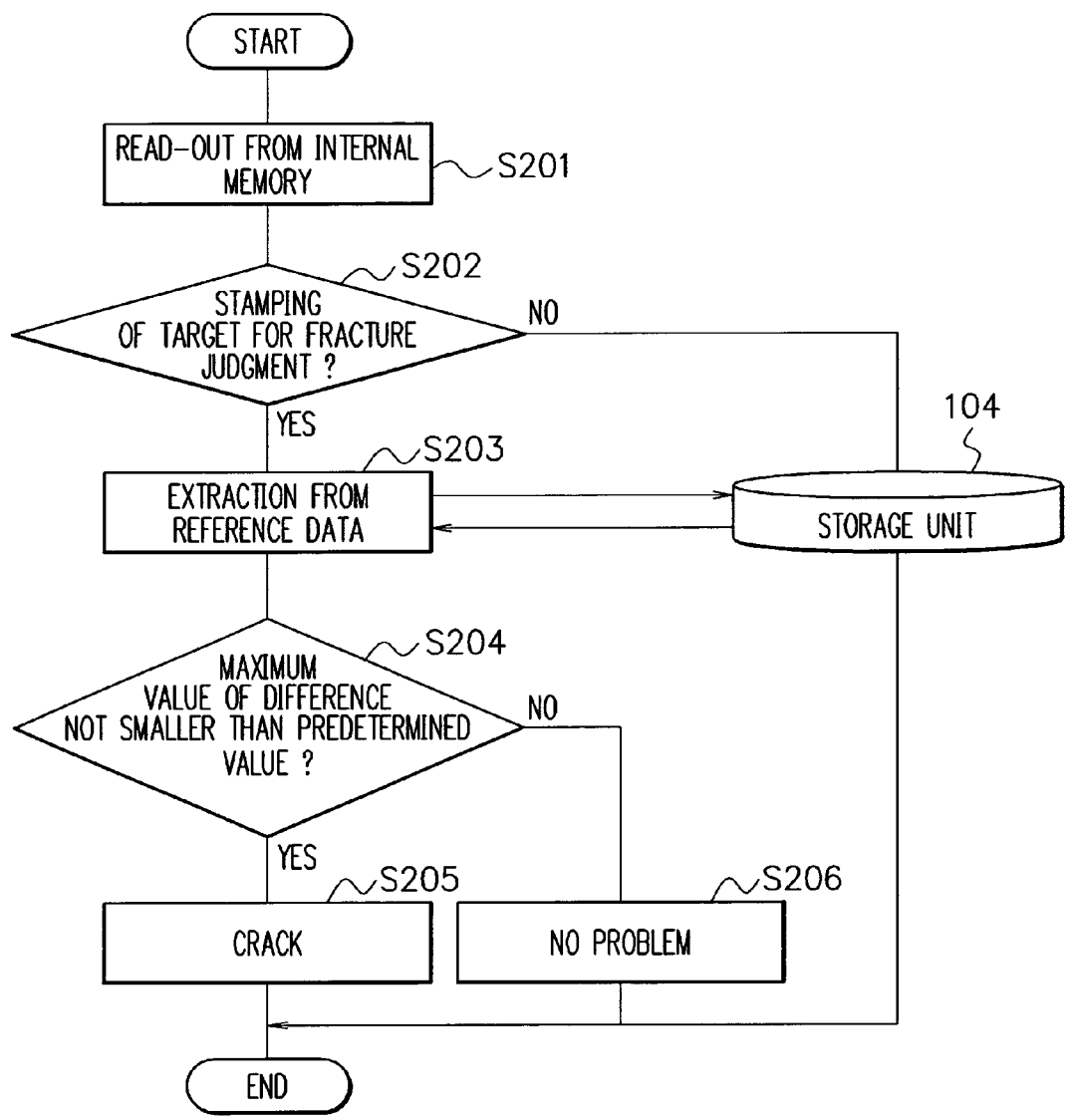
FIG. 3 is a flow chart regarding judgment of fracture.

FIG. 2 is a flow chart regarding measurement of strain of the target die to be measured, and acquisition of the production conditions. FIG. 3 is a flow chart regarding fracture judgment.

First, the flow chart in FIG. 2 will be explained.

In step S101 (process for judging start of stamping), whether stamping started or not is judged. The start of stamping herein is judged if a slide of the stamping press held at a stand-by position started to operate, and advanced to the position of touch between the upper and lower dies. When a work is set at a regular position of the lower die, and the slide advances to the position of touch between the upper and lower dies, the work is clamped by the upper and lower dies, and the stamping begins. If there is no work set on the lower die, the stamping of work does not start even if the slide advances to the position of touch between the upper and lower dies.

The advancement of the slide to the position of touch between the upper and lower dies and the start of stamping of work may not synchronize, typically also when the work is set on the lower die off-aligned with respect to the regular position. Even in this case, a judgment of "Stamping started?=YES" is always given if the slide of the stamping press advances to the position of touch between the upper and lower dies, so as to proceed the process.

One possible method of judging whether the stamping started, that is, whether the slide advanced to the position of touch between the upper and lower dies, may be such as preliminarily finding the angle of a crank of the stamping press or the position of the slide of the stamping press, which corresponds to the position of touch between the upper and lower dies, and providing a mechanism such as a relay which generates a signal when the slide reaches the position, so as to place a judgment of "stamping started" if the signal is received. Another possible method may be such as monitoring output signals from the strain measuring units 8 provided to the target die to be measured, and judging the start of stamping, while assuming that the timing at which the output elevates up to a predetermined level corresponds to the position of touch between the upper and lower dies.

If a judgment of "Stamping started?=NO" is placed, the judgment is repeated until "Stamping started?=YES" is given.

In step S102 (measurement of amount of strain of die), the amount of strain of die set as the target die to be measured is measured by the strain measuring units 8.

In step S103 (acquisition of production conditions), production conditions including at least sliding speed is acquired out of production conditions including production time, ambient temperature, humidity, sliding speed, blank holding force, lot number of work, blank process position information traceable from material lot, tensile strength of work, yield strength of work, amount of uniform elongation of work, and thickness of work.

The lot number of work herein is a lot number given when the work was manufactured by a material manufacture or the like. For an exemplary case of sheet metal wound up into a coil form, it may be a coil management number or the like corresponds to the lot number.

The blank process position information traceable from material lot means information about which portion of a work of a single lot typically manufactured by a material manufacturer was the blank obtained from by processing. For an exemplary case of sheet metal shipped after wound up into a coil, the information is useful for understanding from which portion of the coil the blank was cut. More specifically, the information may be such as representing position of cutting of blank x [m] in a coordinate system having the origin defined at the top of the coil and having the x-direction defined in the direction of rolling, or, may be such as representing position of cutting y [m] (position in the width-wise direction of the coil) in a coordinate system having the y-axis defined normal to the x-direction in the above-described coordinate system.

In step S104 (process for judging completion of stamping), whether the stamping completed or not is judged. A judgment of completion of stamping herein is placed, when the slide of the stamping press, once reached the bottom dead position of stamping and then turned into reverse operation, returned back to the start position of stamping. Definition of the start position is same as that described in step S101.

One possible method of judging whether the stamping completed, that is, whether the slide returned back to the start position of stamping, may be such as preliminarily finding the angle of a crank of the stamping press or the position of the slide of stamping press, which corresponds to the completion of stamping, and providing a mechanism such as a relay which generates a signal when the slide reaches the position, so as to place a judgment of "stamping completed" if the signal is received.

Another possible method may be such as using information of sliding speed acquired in step S103. In this method, a judgment of "stamping completed" is placed upon elapse of a certain calculated time after the start time of stamping, since the time of completion of stamping may readily be calculated if the slide of the stamping press is preliminarily known to operate according to a sine curve, and the sliding speed at the beginning of the stamping is given.

If a judgment of "Stamping completed?=NO" is placed, step S102 and step S103 are repeated until "Stamping completed?=YES" is placed.

Since the crack generation in the process of stamping is a phenomenon generally occurs within a time as very short as several milliseconds, so that also step S102 is preferably repeated at a cycle of repetition of several milliseconds or shorter. Measurement at a sampling rate of 1 KHz or higher is preferable, if it is acceptable by the performance of processing of a measuring instrument.

The cycle of repetition of step S103 may be synchronous to, or unsynchronous to process 102. Out of production conditions, since production time, lot number of work, blank process position information traceable from material lot, tensile strength of work, yield strength of work, amount of uniform elongation of work, thickness of work and so forth are supposed to hardly vary within a single cycle, and may therefore be measured once at an appropriate time in the cycle of repetition, such as in the first cycle or in the last cycle.

In step S105 (storage in internal memory), strain of the target die to be measured over the duration from the start time of stamping to finishing time of stamping, which was acquired by the preceding process, and, production conditions are stored in an internal memory, such as a memory of a computer.

Next, the flow chart in FIG. 3 will be explained.

In step S201 (Read-out from internal memory), data over the duration of time from the start time of stamping to the finishing time of stamping (strain of the target die to be measured, and production conditions), which are stored in the internal memory referring to the above-described flow chart in FIG. 2, are read out.

In step S202 (judgment of target stamping for fracture judgment), whether the data read out from the internal memory device in step S201 is that of the target stamping for fracture judgment or not, is judged. If the data is that of the target stamping for fracture judgment, the data over the duration from the start time of stamping to the finishing time of stamping is defined as the target data for fracture judgment, and the process advances to step S203. If the data is not that of the target stamping for fracture judgment, production conditions which are preliminarily proven that no crack generates thereunder are stored, as the reference data, in the storage unit 104.

In step S203 (extraction from the reference data), out of the reference data stored in the storage unit 104, the reference data which satisfies a predetermined condition is extracted as the comparative data, based on the production conditions of the target data for fracture judgment which was read out from the internal memory device in step S201. One specific method may be such as extracting the reference data, which gives the minimum total of differences between the production conditions of the reference data extracted from the storage unit 104 and the production conditions of the target data for fracture judgment, as the comparative data.

If there is only one production condition of the target data for fracture judgment, data stored in the storage unit 104 are ascended with respect to the production condition, and a data which is nearest in value of the production condition (that is, a data giving the minimum difference) is extracted as the comparative data. If there are a plurality of data having the same production condition stored in the storage unit 104, a file having the latest time of storage, out of the plurality of data, is preferably extracted as the production conditions. Alternatively, one data may randomly be extracted typically by using a random number, in place of using the time of storage.

If there are two or more production conditions of the target data for fracture judgment, a data which is nearest in values of the production conditions is extracted as the comparative data, according to the procedures below. Considering now a case where three production conditions A, B, C are measured as the target data for fracture judgment Xt. Values of the production condition A, production condition B, and production condition C are denoted as At, Bt and Ct, respectively. First, of the data stored in the storage unit 104, proximity dAi between the i-th data Xi and the target data for fracture judgment Xt with respect to the production conditions A is defined by the equation (1) below:

$$dAi = \alpha A \cdot (Ai - At)/At \qquad (1)$$

where Ai is a value of production conditions A of the data Xi. $\alpha A$ is a weighting coefficient, and is basically set to 1, but may arbitrarily be modified depending on the importance of the production conditions to be concerned.

Also production conditions B and C are similarly defined.

$$dBi = \alpha B \cdot (Bi - Bt)/Bt \qquad (2)$$

$$dCi = \alpha C \cdot (Ci - Ct)/Ct \qquad (3)$$

Proximity di between the i-th data Xi and the target data for fracture judgment Xt with respect to the production conditions A, B and C is defined by the equation (4) below:

$$di = dAi + dBi + dCi \qquad (4)$$

Such di is calculated with respect to the entire data stored in the storage unit 104, and the data which gives di most close to zero is extracted as the data having the nearest production conditions.

Since the equations (1) to (3) result in impossible if At; Bt or Ct is zero, it may be necessary to take some measure such as converting the unit system so as not to give zero, or such as adding a constant. More specifically, for example, if the temperature out of the production conditions is expressed in Fahrenheit rather than in Celsius, the equations (1) to (3) may be turned possible even if the ambient temperature falls to zero in the wintertime. In another exemplary case where the lot number of work, expressed in 6-digit number, may have a value of "000000" or the like, the equations (1) to (3) may always be kept possible, without causing division by zero, by adding "100000" to the lot number.

Besides them, it is also possible to extract the nearest data using various cluster analytical methods, and more specifically methods of hierarchical cluster analysis such as the nearest neighbor method, furthest neighbor method, group average method, and Ward's method; or, non-hierarchical clustering technique such as K-means.

In step S204 (judgment of whether a predetermined condition is satisfied or not), the strain of the comparative data extracted in step S203 and the strain of the target data for fracture judgment are compared, and whether a predetermined condition is satisfied or not is judged. One specific method is such as judging whether the maximum value of difference between the strain of the extracted comparative data and the strain of the target data for fracture judgment is not smaller than a predetermined value or not. The strain may be obtained as a waveform data, wherein the difference of the waveform data is obtained by comparing strain value of the reference data with strain value of the target data for fracture judgment at same positions in the stroke. The differences are obtained for all positions in the stroke, and a difference having the largest absolute value is defined as the maximum value of difference. Another possible method may be such as sampling a plurality of differences between the strain of the comparative data and the strain of the target data for fracture judgment at same positions of stroke, and then judging whether a sum of squares of the differences is not smaller than a predetermined value or not. Still another possible method may be such as obtaining difference between the strain of the comparative data and the strain of the target data for fracture judgment as a waveform data, and then judging whether the primary differential coefficient or secondary differential coefficient is not smaller than a predetermined value or not.

If the result of judgment in step S204 is YES, the process advances to step S205 to place a judgment of "crack occurred" in the stamped product. If the result of judgment in step S204 is NO, the process advances to step S206 to place a judgment of "no problem". As for the stamped product judged herein as "no problem", the strain of the target die to be measured over the duration from the start time of stamping to the finishing time of stamping, and, the production conditions may be stored as the reference data in the storage unit 104.

In the above-described embodiment, the duration from the start time of stamping to the finishing time of stamping has been defined as the target duration to be judged used in the extraction step. In contrast, also a method of adopting the duration from the start time of stamping up to the time when the stamping proceeds beyond a predetermined range of the stroke of stamping, may be defined as the target duration to be judged used in the extraction step.

By limiting the duration to be judged in this way, an effect of precise judgment while excluding any influences of external disturbance may be obtained. Also volume of data may be decreased, and thereby rate of processing may be increased.

Second Embodiment

In a second embodiment, the duration from the start time of stamping up to the time when the stamping proceeds by at least 30% or more of the stroke of stamping, is defined as the target duration to be judged. Since the fracture judgment apparatus 100 and basic processing operations thereof are same as those described in the first embodiment, so that the explanation below will be given mainly on aspects different from those in the first embodiment.

In the second embodiment, the flow chart regarding measurement of the strain of the target die to be measured and the acquisition of the production conditions is same as explained in FIG. 2. In this embodiment, the duration from the start time of stamping to the finishing time of stamping may be targeted at, or the duration from start time of stamping up to the time when the stamping proceeds by at least 30% or more of the stroke of stamping may be targeted at.

FIG. 4 is a flow chart regarding fracture judgment. The flow chart illustrated in FIG. 4 is similar to FIG. 3, except that the duration from the start time of stamping up to the time when the stamping proceeds by at least 30% or more is targeted at, and that two processes (step S301, S302) described below are added to the flow chart in FIG. 3. The explanation will be given below mainly on aspects different from those in FIG. 3.

In step S203 (extraction from the reference data), out of the reference data stored in the storage unit 104, the reference data which is nearest to the production conditions of the target data for fracture judgment over the duration from the start time of stamping up to the time when the stamping proceeds by at least 30% or more of the stroke of stamping, read out from the internal memory device in step S201, is extracted as the comparative data. More specifically, the reference data, which gives the minimum total of differences between the production conditions of the reference data extracted from the storage unit 104 and the production conditions of the target data for fracture judgment, is extracted as the comparative data.

In step S301 (judgment of blankless stamping), out of the data extracted in step S203, a maximum value of strain of the comparative data and a maximum value of strain of the target data for fracture judgment are compared, over the duration from the start time of stamping up to the time when the stamping proceeds by at least 30% or more of the stroke of stamping. If, as a consequence, the maximum value of strain of the target data for fracture judgment is smaller than 20% of the maximum value of strain of the comparative data, the process advances to step S302 so as to place a judgment of "blankless stamping", and to except the value from the fracture judgment. In contrast, the process advances to step S204 for fracture judgment, only when the maximum value of strain of the target data for fracture judgment was found to be not smaller than 20% of the maximum value of strain of the comparative data.

Third Embodiment

Also in a third embodiment, the duration from the start time of stamping up to the time when the stamping proceeds by at least 30% or more of the stroke of stamping, is defined as the target duration to be judged, similarly to as in the second embodiment. Since the fracture judgment apparatus 100 and basic processing operations thereof are same as those described in the first embodiment, so that the explanation below will be given mainly on aspects different from those in the first embodiment.

In the third embodiment, the flow chart regarding measurement of the strain of the target die to be measured and the acquisition of the production conditions is same as explained in FIG. 2. In this embodiment, the duration from the start time of stamping to the finishing time of stamping may be targeted at, or the duration from start time of stamping up to the time when the stamping proceeds by at least 30% or more of the stroke of stamping, may be targeted at.

FIG. 5 is a flow chart regarding fracture judgment. The flow chart illustrated in FIG. 5 is similar to FIG. 3, except that the duration from the start time of stamping up to the time when the stamping proceeds by at least 30% or more of the stroke of stamping is targeted at, and that two processes (step S401, S402) described below are added to the flow chart in FIG. 3. The explanation will be given below mainly on aspects different from those in FIG. 3.

In step S203 (extraction from the reference data), similarly to as described in the second embodiment, out of the reference data stored in the storage unit 104, the reference data which is nearest to the production conditions of the target data for fracture judgment over the duration from the start time of stamping up to the time when the stamping proceeds by at least 30% or more of the stroke of stamping, read out from the internal memory device in step S201, is extracted as the comparative data. More specifically, the reference data, which gives the minimum total of differences between the production conditions of the reference data extracted from the storage unit 104 and the production conditions of the target data for fracture judgment, is extracted as the comparative data.

In step S401 (judgment of abnormal measurement), out of the data extracted in step S203, a strain waveform of the comparative data, and a strain waveform of the target data for fracture judgment are compared, over the duration from the start time of stamping up to the time when the stamping proceeds by at least 30% or more of the stroke of stamping. If, as a consequence, a correlation coefficient of the strain waveform of the comparative data and the strain waveform of the target data for fracture judgment is smaller than 0.6, the process advances to step S402 so as to place a judgment of "abnormal measurement", and excepts it from the fracture judgment. In contrast, the process advances to step S204 for fracture judgment, only when the correlation coefficient of the strain waveform of the comparative data and the strain waveform of the target data for fracture judgment is 0.6 or larger. A method of calculating the correlation coefficient basically conforms to a method of calculating Pearson's product-moment correlation coefficient.

Fourth Embodiment

In a fourth embodiment, the duration from the time when the stamping proceeds by at least 60% of the stroke of stamping from the start time of stamping, up to the time when a reverse operation of a slide of a stamping press, after reaching the bottom dead position of stamping and turning into the reverse operation, proceeds by at least 20% or more of a stroke of stamping from the bottom dead position, is defined as the target duration to be judged. Since the fracture judgment apparatus 100 and basic processing operations thereof are same as those described in the first embodiment, so that the explanation below will be given mainly on aspects different from those in the first embodiment.

In the fourth embodiment, the flow chart regarding measurement of the strain of the target die to be measured and the acquisition of the production conditions is same as explained in FIG. 2. In this embodiment, the duration from the start time of stamping to the finishing time of stamping may be targeted at, or the duration from the time when the stamping proceeds by at least 60% of the stroke of stamping from the start time of stamping, up to the time when a reverse operation of a slide of a stamping press, after reaching the bottom dead position of stamping and turning into the reverse operation, proceeds by at least 20% or more of a stroke of stamping from the bottom dead position, may be targeted at.

In step S203 (extraction from the reference data), out of the reference data stored in the storage unit 104, the reference data which is nearest to the production conditions of the target data for fracture judgment over the duration from the time when the stamping proceeds by at least 60% of the stroke of stamping from the start time of stamping, up to the time when a reverse operation of a slide of a stamping press, after reaching the bottom dead position of stamping and turning into the reverse operation, proceeds by at least 20% or more of a stroke of stamping from the bottom dead position, read out from the internal memory device in step S201, is extracted as the comparative data. More specifically, the reference data, which gives the minimum total of differences between the production conditions of the reference data extracted from the storage unit 104 and the production conditions of the target data for fracture judgment, is extracted as the comparative data.

Fifth Embodiment

Also in a fifth embodiment, the duration from the time when the stamping proceeds by at least 60% of the stroke of stamping from the start time of stamping, up to the time when a reverse operation of a slide of a stamping press, after reaching the bottom dead position of stamping and turning into the reverse operation, proceeds by at least 20% or more of a stroke of stamping from the bottom dead position, is defined as the target duration to be judged, similarly to as in the fourth embodiment. Since the fracture judgment apparatus 100 and basic processing operations thereof are same as those described in the first embodiment, so that the explanation below will be given mainly on aspects different from those in the first embodiment.

In the fifth embodiment, the flow chart regarding measurement of the strain of the target die to be measured and the acquisition of the production conditions is same as explained in FIG. 2. In this embodiment, the duration from the start time of stamping to the finishing time of stamping may be targeted at, or the duration from the time when the stamping proceeds by at least 60% of the stroke of stamping from the start time of stamping, up to the time when a reverse operation of a slide of a stamping press, after reaching the bottom dead position of stamping and turning into the reverse operation, proceeds by at least 20% or more of a stroke of stamping from the bottom dead position, may be targeted at.

Processes in the flow chart regarding the fracture judgment are similar to those explained referring to FIG. 5, except for steps S203 and S401.

In step S203 (extraction from the reference data), similarly to as described in the fourth embodiment, out of the reference data stored in the storage unit 104, the reference data which is nearest to the production conditions of the target data for fracture judgment, over the duration from the time when the stamping proceeds by at least 60% of the stroke of stamping from the start time of stamping, up to the time when a reverse operation of a slide of a stamping press, after reaching the bottom dead position of stamping and turning into the reverse operation, proceeds by at least 20% or more of a stroke of stamping from the bottom dead position, read out from the internal memory device in step S201, is extracted as the comparative data. More specifically, the reference data, which gives the minimum total of differences between the production conditions of the reference data extracted from the storage unit 104 and the production conditions of the target data for fracture judgment, is extracted as the comparative data.

In step S401 (judgment of abnormal measurement), out of the data extracted in step S203, a strain waveform of the comparative data, and a strain waveform of the target data for fracture judgment are compared, over the duration from the time when the stamping proceeds by at least 60% of the stroke of stamping from the start time of stamping, up to the time when a reverse operation of a slide of a stamping press, after reaching the bottom dead position of stamping and turning into the reverse operation, proceeds by at least 20% or more of a stroke of stamping from the bottom dead position. If, as a consequence, a correlation coefficient of the strain waveform of the comparative data and the strain waveform of the target data for fracture judgment is smaller than 0.6, the process advances to step S402 so as to place a judgment of "abnormal measurement", and excepts it from the fracture judgment. In contrast, the process advances to step S204 for fracture judgment, only when the correlation coefficient of the strain waveform of the comparative data and the strain waveform of the target data for fracture judgment is 0.6 or larger. A method of calculating the correlation coefficient basically conforms to a method of calculating Pearson's product-moment correlation coefficient.

Example 1

As Example 1 of the present invention, the fracture judgment of stamped products was carried out according to the flow charts illustrated in FIG. 2 and FIG. 3 in the first embodiment. Characteristics of a steel sheet used as the work are listed in Table 1. The steel sheet used herein has a thickness of 1.8 mm, and a tensile strength of 590 MPa-class.

TABLE 1

| Material | Yield stress [MPa] | Tensile strength [MPa] | Elongation [%] |
|---|---|---|---|
| Steel sheet | 378 | 608 | 35 |

First, applied states of the flow chart in FIG. 2 will be explained. In step S101, a method of monitoring signal output from the strain measuring units 8 attached to the target die to be measured, and judging the start of stamping, while assuming the time when the output elevates up to a predetermined level as the position of touch between the upper and lower dies, was adopted. Piezoelectric elements disposed inside the target die to be measured were used as the strain measuring unit 8.

As for the cycle of repetition of step S102, a sampling rate of 1 [KHz] for the measurement was adopted.

In step S103, combinations of all of eleven production conditions (production time, ambient temperature, humidity, sliding speed, blank holding force, lot number of work, blank process position information traceable from material lot, tensile strength of work, yield strength of work, amount of uniform elongation of work, thickness of work) specified by the present invention were adopted, which were found to be successful in crack detection without causing any problem. Combinations of the production conditions adopted herein, values of weighting coefficient α, correspondent rate of abnormality, rate of normal judgment, rate of excessive detection, and miss rate are listed in Table 2.

In this Example, the cases where three production conditions of production time, sliding speed, and ambient temperature were particularly selected, will be explained.

In the repetitive cycles of step S103, the measurement was made in the first cycle of the repetitive cycles. More specifically, out of three production conditions, the production time means the production time immediately after a judgment of "stamping started" was placed in step S101, and the sliding speed and the ambient temperature mean those at thus-determined production time, that is, the sliding speed and the ambient temperature immediately after the touch of the dies, respectively.

As a method of placing a judgment of "stamping completed" in step S104, that is, a method of judging whether the slide returned back to the start position of stamping or not, adopted herein was a method of placing a judgment of "stamping completed", upon reception of a signal generated when the slide reaches the position represented by an angle of crank of stamping press of 220°, which was found to correspond to the position of completion of stamping.

In step S105, a memory of a computer was used as an internal memory device.

Next, the applied states of the flow chart in FIG. 3 will be explained. First, in order to confirm the functions of the flow chart in FIG. 3, stamping was carried out ten times so as to collect the reference data which are not targeted at the fracture judgment, and another stamping was carried out once so as to obtain the target data for fracture judgment. Details of ten reference data not targeted at the fracture judgment are listed in Table 3. At the beginning, in step S202, whether the process is the target stamping for fracture judgment or not is judged. The production conditions which are confirmed to give no crack generated thereunder, and not targeted at the fracture judgment, are stored in the storage unit 104 as the reference

TABLE 2

| | | Combinations of production conditions (1 = used, 0 = not used) | | | | | | | | | | |
|---|---|---|---|---|---|---|---|---|---|---|---|---|
| | α | N1 | N2 | N3 | N4 | N5 | N6 | N7 | N8 | N9 | N10 | N11 |
| 1 Time of production | 0.1 | 1 | 1 | 1 | 1 | 1 | 1 | 1 | 1 | 1 | 1 | 1 |
| 2 Ambient temperature | 1.0 | 0 | 1 | 1 | 1 | 1 | 1 | 1 | 1 | 1 | 1 | 1 |
| 3 Humidity | 1.0 | 0 | 0 | 1 | 1 | 1 | 1 | 1 | 1 | 1 | 1 | 1 |
| 4 Sliding speed | 1.0 | 0 | 0 | 0 | 1 | 1 | 1 | 1 | 1 | 1 | 1 | 1 |
| 5 Blank holding force | 1.0 | 0 | 0 | 0 | 0 | 1 | 1 | 1 | 1 | 1 | 1 | 1 |
| 6 Lot number of work | 0.2 | 0 | 0 | 0 | 0 | 0 | 1 | 1 | 1 | 1 | 1 | 1 |
| 7 Blank process position information traceable from material lot | 2.0 | 0 | 0 | 0 | 0 | 0 | 0 | 1 | 1 | 1 | 1 | 1 |
| 8 Tensile strength of work | 1.0 | 0 | 0 | 0 | 0 | 0 | 0 | 0 | 1 | 1 | 1 | 1 |
| 9 Yield stress of work | 1.0 | 0 | 0 | 0 | 0 | 0 | 0 | 0 | 0 | 1 | 1 | 1 |
| 10 Amount of uniform elongation of work | 1.0 | 0 | 0 | 0 | 0 | 0 | 0 | 0 | 0 | 0 | 1 | 1 |
| 11 Thickness of work | 1.0 | 0 | 0 | 0 | 0 | 0 | 0 | 0 | 0 | 0 | 0 | 1 |
| Rate of abnormality (number of cracked products/total number of products) [%] | | 1.7 | 1.6 | 1.7 | 1.7 | 1.6 | 1.7 | 1.6 | 1.7 | 1.7 | 1.6 | 1.7 |
| Rate of normal judgment (number of normally judged products/total number of products) [%] | | 1.7 | 1.6 | 1.6 | 1.7 | 1.6 | 1.6 | 1.6 | 1.7 | 1.6 | 1.6 | 1.7 |
| Rate of excessive detection (number of excessively detected products/total number of products) [%] | | 235 | 220 | 210 | 235 | 220 | 210 | 220 | 235 | 211 | 220 | 235 |
| Miss rate (number of missed products/total number of products) [%] | | 123 | 120 | 120 | 123 | 120 | 120 | 120 | 123 | 129 | 120 | 123 | data. If judged as the target stamping for fracture judgment, the process then advances to step S203 and thereafter.

TABLE 3

| | Production conditions | | | |
|---|---|---|---|---|
| No. | Time of production (s) | Ambient temperature (° C.) | Sliding speed [mm/s] | Amount of strain of target die to be measured |
| 1 | 0 | 23.5 | 99 | Data X1 |
| 2 | 3 | 22.9 | 110 | Data X2 |
| 3 | 6 | 22.4 | 103 | Data X3 |
| 4 | 10 | 24.1 | 122 | Data X4 |
| 5 | 14 | 23.7 | 156 | Data X5 |
| 6 | 18 | 26.0 | 175 | Data X6 |
| 7 | 22 | 27.0 | 180 | Data X7 |
| 8 | 26 | 28.8 | 181 | Data X8 |
| 9 | 30 | 30.0 | 176 | Data X9 |
| 10 | 34 | 32.0 | 177 | Data X10 |

In Table 3, data X1 to data X10 are results of measurement of the amount of strain of the target die to be measured. Contents of data X1 are listed in Table 4. The first column represents the time elapsed from the start time of stamping [ms], and the second column represents the amount of strain of the target die to be measured [pc]. As for data X1, measurement was carried out up to an elapsed time of 1500 [ms] from the start time of stamping, since the sliding speed is 99 [mm/s], and the sampling rate of measurement is 1 [KHz].

TABLE 4

| Time elapsed from start of stamping [ms] | Amount of strain of target die to be measured [με] |
|---|---|
| 1 | 0 |
| 2 | 10 |
| 3 | 22 |
| 4 | 34 |
| 5 | 44 |
| 6 | 56 |
| ... | ... |
| 1492 | 23 |
| 1493 | 20 |
| 1494 | 15 |
| 1495 | 10 |
| 1496 | 7 |
| 1497 | 3 |
| 1498 | 0 |
| 1499 | 0 |
| 1500 | 0 |

Next, the target data for fracture judgment for a single time is listed in Table 5. The contents of the target data for fracture judgment are same as the reference data listed in Table 3 or Table 4.

TABLE 5

| | Production conditions | | | |
|---|---|---|---|---|
| | Time of production (s) (=A) | Ambient temperature [° C.] (=B) | Sliding speed [mm/s] (=C) | Amount of strain of target die to be measured |
| Target data for fracture judgment Xt | 60 | 23 | 150 | Data Xt |

Using now the equations (1) to (4), a data nearest to the target data for fracture judgment listed in Table 4 in the above is extracted from the reference data listed in Table 2. First, three weighting coefficients αA, αB and αC, used for the equations (1) to (3), are those listed in Table 6.

TABLE 6

| | αA (Time of production) | αB (Ambient temperature) | αC (Sliding speed) |
|---|---|---|---|
| α | 0.1 | 1 | 1 |

Next, results of calculation of each of ten reference data listed in Table 3, obtained using the equations (1) to (4), are listed in Table 7.

TABLE 7

| i | dAi | dBi | dCi | di |
|---|---|---|---|---|
| 1 | 0.10 | −0.02 | 0.34 | 0.42 |
| 2 | 0.10 | 0.00 | 0.27 | 0.37 |
| 3 | 0.09 | 0.03 | 0.31 | 0.43 |
| 4 | 0.08 | −0.05 | 0.19 | 0.22 |
| 5 | 0.08 | −0.03 | −0.04 | 0.01 |
| 6 | 0.07 | −0.13 | −0.17 | −0.23 |
| 7 | 0.06 | −0.17 | −0.20 | −0.31 |
| 8 | 0.06 | −0.25 | −0.21 | −0.40 |
| 9 | 0.05 | −0.30 | −0.17 | −0.43 |
| 10 | 0.04 | −0.39 | −0.18 | −0.53 |

As is obvious from Table 7, the data giving di nearest to zero is i=5 (No. 5 in Table 3), so that data No. 5 was extracted as the target data for fracture judgment, and was defined as the comparative data.

Next, in step S205, difference between the comparative data No. 5 extracted in the above and the target data for fracture judgment was calculated, and whether the maximum value of difference is not smaller than a predetermined value or not was judged. The predetermined value herein was set to 30 [pc].

Actually, the stamping, not targeted at the fracture judgment, was carried out 5,000 times, similarly according to the procedures described in the above. Data collected therefrom were stored in the storage unit 104. The storage unit 104 used herein was a hard disk of a computer.

Next, the target stamping for fracture judgment was carried out 100,000 times. The nearest data was extracted similarly according to the procedures described in the above for each of 100,000 times of stamping, the difference in strain with respect to the extracted data was calculated, and whether the maximum value of difference is equal to or larger than a predetermined value of 30 [pc] was judged. Results of calculation are listed in Table 8. It is understood that the crack detection is highly accurate, showing a rate of normal judgment of 1.64%, with a rate of excessive detection of 230 [ppm], and a miss rate of 110 [ppm].

TABLE 8

|  |  |  | Total number of products | Number of normal products | Number of cracked products |
|---|---|---|---|---|---|
| Results of product inspection |  |  | 100000 | 98345 | 1655 |
| Rate of abnormality (number of cracked products/total number of products) [%] |  |  |  | 1.66% |  |
| Judgment criteria 1 | Judgment by strain measuring unit |  | 100000 | 98333 | 1667 |
|  | Details of abnormal judgment | Normal judgment (results of product inspection coincide with judgment) |  |  | 1644 |
|  |  | Excessive detection |  |  | 23 |
|  |  | Missing |  |  | 11 |
|  | Rate of normal judgment (number of normally judged products/total number of products) [%] |  |  | 1.64% |  |
|  | Rate of excessive detection (number of excessively detected products/total number of products) [ppm] |  |  | 230.0 |  |
|  | Miss rate (number of missed products/total number of products) [ppm] |  |  | 110.0 |  |

Example 2

As Example 2 of the present invention, the fracture judgment of stamped products was carried out according to the flow charts illustrated in FIG. 2 and FIG. 3 in the first embodiment. In this Example, the piezoelectric elements, as the strain measuring units 8, were disposed to the punch and the blank holding die. It was confirmed that the fracture judgment was successfully normal in all trials of disposition of the strain measuring units 8 in all possible combinations of the punch, the die and the blank holding die, although the description herein only deals with the cases where the strain measuring units 8 were disposed to the punch and the blank holding die.

Characteristics of a steel sheet used as the work are listed in Table 1. Also the methods of application of the flow charts illustrated in FIG. 2 and FIG. 3 are same as described in Example 1.

Actually, the stamping, for obtaining the reference data but not targeted at the fracture judgment, was carried out 5,000 times, similarly according to the procedures described in the above. Data collected therefrom were stored in the storage unit 104. The storage unit 104 used herein was a hard disk of a computer.

Next, the target stamping for fracture judgment was carried out 100,000 times. The nearest data was extracted similarly according to the procedures described in the above for each of 100,000 times of stamping, the difference in strain with respect to the comparative data was calculated, and whether the maximum value of difference is equal to or larger than a predetermined value (30 [µε]) was judged. Results of calculation are listed in Table 9. It is understood that the crack detection is highly accurate, showing a rate of normal judgment of 1.64%, with a rate of excessive detection of 220 [ppm], and a miss rate of 160 [ppm].

TABLE 9

|  |  |  | Total number of products | Number of normal products | Number of cracked products |
|---|---|---|---|---|---|
| Results of product inspection |  |  | 100000 | 98340 | 1660 |
| Rate of abnormality (number of cracked products/total number of products) [%] |  |  |  | 1.66% |  |
| Judgment criteria 1 | Judgment by strain measuring unit |  | 100000 | 98334 | 1666 |
|  | Details of abnormal judgment | Normal judgment (results of product inspection coincide with judgment) |  |  | 1644 |
|  |  | Excessive detection |  |  | 22 |
|  |  | Missing |  |  | 16 |
|  | Rate of normal judgment (number of normally judged products/total number of products) [%] |  |  | 1.64% |  |
|  | Rate of excessive detection (number of excessively detected products/total number of products) [ppm] |  |  | 220.0 |  |
|  | Miss rate (number of missed products/total number of products) [ppm] |  |  | 160.0 |  |

Example 3

As Example 3 of the present invention, the fracture judgment of stamped products was carried out according to the flow charts illustrated in FIG. 2 and FIG. 4 in the second embodiment. Characteristics of a steel sheet used as the work are listed in Table 1. Also the method of application of the flow chart illustrated in FIG. 2 is same as described in Example 1. The measurement of strain of the dies is same as described in Example 1. Also the methods of application of the flow chart in FIG. 2 is same as described in Example 1.

Also for the flow chart in FIG. 4, the processes are similar to those described in Example 1, except for step S203 and step S301, so that the description herein will be given only on the methods of application of step S203 and step S301.

In step S203 (extraction from the reference data), out of the reference data stored in the storage unit 104, the reference data, which gives the minimum total of differences between the production conditions of the reference data extracted from the storage unit 104 and the production conditions of the target data for fracture judgment, over the duration from the start time of stamping up to the time when the stamping proceeds by at least 30% or more of the stroke of stamping, read out from the internal memory device in step S201, is extracted as the comparative data. A specific method of calculating the minimum total of the differences in the production conditions is same as described in Example 1.

In step S301 (judgment of blankless stamping), out of the data extracted in step S203, a maximum value of strain of the comparative data and a maximum value of strain of the target data for fracture judgment are compared, over the duration from the start time of stamping up to the time when the stamping proceeds by at least 30% or more of the stroke of stamping. If, as a consequence, the maximum value of strain of the target data for fracture judgment is smaller than 20% of the maximum value of strain of the comparative data, the process advances to step S302 so as to place a judgment of "blankless stamping", and to except the value from the fracture judgment. In contrast, the fracture judgment takes place only when the maximum value of strain of the target data for fracture judgment was found to be not smaller than 20% of the maximum value of strain of the comparative data.

Actually, the stamping, for obtaining the reference data but not targeted at the fracture judgment, was carried out 5,000 times, similarly according to the procedures described in the above. Data collected therefrom were stored in the storage unit 104. The storage unit 104 used herein was a hard disk of a computer.

Next, the target stamping for fracture judgment was carried out 100,000 times. The nearest data was extracted similarly according to the procedures described in the above for each of 100,000 times of stamping, the difference in strain with respect to the comparative data was calculated, and whether the maximum value of difference is equal to or larger than a predetermined value (30 [µε]) is judged. Results of calculation are listed in Table 10. It is understood that the crack detection is highly accurate, showing a rate of normal judgment of 1.63%, with a rate of excessive detection of 120 [ppm], and a miss rate of 260 [ppm]. At the same time, it is understood that the cracks are precisely detected also for the blankless stamping, without causing excessive detection and missing.

TABLE 10

|  |  | Total number of products | Number of normal products | Number of cracked products | Judgment of blankless stamping |
|---|---|---|---|---|---|
| Results of product inspection |  | 100000 | 98090 | 1660 | 250 |
| Rate of abnormality (number of cracked products/total number of products) [%] |  |  | 1.66% |  |  |
| Judgment criteria 1 | Judgment by strain measuring unit | 100000 | 98104 | 1646 | 250 |
|  | Details of abnormal judgment | Normal judgment (results of product inspection coincide with judgment) |  | 1634 | 250 |
|  |  | Excessive detection |  | 12 | 0 |
|  |  | Missing |  | 26 | 0 |
|  | Rate of normal judgment (number of normally judged products/total number of products) [%] |  |  | 1.63% | 0.25% |
|  | Rate of excessive detection (number of excessively detected products/total number of products) [ppm] |  |  | 120.0 | 0.0 |
|  | Miss rate (number of missed products/total number of products) [ppm] |  |  | 260.0 | 0.0 |

Example 4

As Example 4 of the present invention, the fracture judgment of stamped products was carried out according to the flow charts illustrated in FIG. 2 and FIG. 5 in the third embodiment. Characteristics of a steel sheet used as the work are listed in Table 1. The measurement of strain of the dies is same as described in Example 1. Also the methods of application of the flow chart in FIG. 2 is same as described in Example 1.

In step S203 (extraction from the reference data), out of the reference data stored in the storage unit 104, the reference data, which gives the minimum total of differences between the production conditions of the reference data extracted from the storage unit 104 and the production conditions of the target data for fracture judgment, over the duration from the start time of stamping up to the time when the stamping proceeds by at least 30% or more of the stroke of stamping, read out from the internal memory device in step S201, is extracted as the comparative data. A specific method of calculating the minimum total of the differences in the production conditions is same as described in Example 1.

In step S401 (judgment of abnormal measurement), out of the data extracted in step S203, a strain waveform of the comparative data, and a strain waveform of the target data for fracture judgment are compared, over the duration from the start time of stamping up to the time when the stamping proceeds by at least 30% or more of the stroke of stamping. If, as a consequence, a correlation coefficient of the strain waveform of the comparative data and the strain waveform of the target data for fracture judgment is smaller than 0.6, a judgment of "abnormal measurement" is placed, and the data is excepted from the fracture judgment. In contrast, the fracture judgment is carried out only when the correlation coefficient of the strain waveform of the comparative data and the strain waveform of the target data for fracture judgment is 0.6 or larger. A method of calculating the correlation coefficient basically conforms to a method of calculating Pearson's product-moment correlation coefficient.

Actually, the stamping, for obtaining the reference data not targeted at the fracture judgment, was carried out 5,000 times, similarly according to the procedures described in the above. Data collected therefrom were stored in the storage unit 104. The storage unit 104 used herein was a hard disk of a computer.

Next, the target stamping for fracture judgment was carried out 100,000 times. The nearest data was extracted similarly according to the procedures described in the above for each of 100,000 times of stamping, the difference in strain with respect to the comparative data was calculated, and whether the maximum value of difference is equal to or larger than a predetermined value (30 [µε]) is judged. Results of calculation are listed in Table 10. It is understood that the crack detection is highly accurate, showing a rate of normal judgment of 1.63%, with a rate of excessive detection of 110 [ppm], and a miss rate of 280 [ppm]. At the same time, it is understood that the cracks are precisely detected also in the judgment of abnormal measurement, without causing excessive detection and missing.

TABLE 11

|  |  |  | Total number of products | Number of normal products | Number of cracked products | Judgment of abnormal measurement |
|---|---|---|---|---|---|---|
| Results of product inspection |  |  | 100000 | 98320 | 1660 | 20 |
| Rate of abnormality (number of cracked products/total number of products) [%] |  |  |  | 1.66% |  |  |
| Judgment criteria 1 | Judgment by strain measuring unit |  | 100000 | 98337 | 1643 | 20 |
|  | Details of abnormal judgment | Normal judgment (results of product inspection coincide with judgment) |  |  | 1632 | 20 |
|  |  | Excessive detection |  |  | 11 | 0 |
|  |  | Missing |  |  | 28 | 0 |
| Rate of normal judgment (number of normally judged products/total number of products) [%] |  |  |  |  | 1.63% | 0.02% |
| Rate of excessive detection (number of excessively detected products/total number of products) [ppm] |  |  |  |  | 110.0 | 0.0 |
| Miss rate (number of missed products/total number of products) [ppm] |  |  |  |  | 280.0 | 0.0 |

Example 5

As Example 5 of the present invention, the fracture judgment of stamped products was carried out according to the flow charts illustrated in FIG. 2 and FIG. 3 in the fourth embodiment. Characteristics of a steel sheet used as the work are listed in Table 1. The measurement of strain of the dies is same as described in Example 1. Also the methods of application of the flow chart in FIG. 2 is same as described in Example 1.

In step S203 (extraction from the reference data), out of the reference data stored in the storage unit 104, the reference data, which gives the minimum total of differences between the production conditions of the reference data extracted from the storage unit 104 and the production conditions of the target data for fracture judgment, over the duration from the time when the stamping proceeds by at least 60% of the stroke of stamping from the start time of stamping, up to the time when a reverse operation of a slide of a stamping press, after reaching the bottom dead position of stamping and turning into the reverse operation, proceeds by at least 20% or more of a stroke of stamping from the bottom dead position, read out from the internal memory device in step S201, is extracted as the comparative data. A specific method of calculating the minimum total of the differences in the production conditions is same as described in Example 1.

Actually, the stamping, for obtaining the reference data not targeted at the fracture judgment, was carried out 5,000 times, similarly according to the procedures described in the above. Data collected therefrom were stored in the storage unit 104. The storage unit 104 used herein was a hard disk of a computer.

Next, the target stamping for fracture judgment was carried out 100,000 times. The nearest data was extracted similarly according to the procedures described in the above for each of 100,000 times of stamping, the difference in strain with respect to the comparative data was calculated, and whether the maximum value of difference is equal to or larger than a predetermined value (30 [$\mu\varepsilon$]) is judged. Results of calculation are listed in Table 12. It is understood that the crack detection is highly accurate, showing a rate of normal judgment of 1.66%, with a rate of excessive detection of [ppm], and a miss rate of 20 [ppm].

TABLE 12

| | | | Total number of products | Number of normal products | Number of cracked products |
|---|---|---|---|---|---|
| Results of product inspection | | | 99980 | 98320 | 1660 |
| Rate of abnormality (number of cracked products/total number of products) [%] | | | | 1.66% | |
| Judgment criteria 1 | Judgment by strain measuring unit | | 99996 | 98337 | 1659 |
| | Details of abnormal judgment | Normal judgment (results of product inspection coincide with judgment) | | | 1658 |
| | | Excessive detection | | | 1 |
| | | Missing | | | 2 |
| | Rate of normal judgment (number of normally judged products/total number of products) [%] | | | | 1.66% |
| | Rate of excessive detection (number of excessively detected products/total number of products) [ppm] | | | | 10.0 |
| | Miss rate (number of missed products/total number of products) [ppm] | | | | 20.0 |

Example 6

As Example 6 of the present invention, the fracture judgment of stamped products was carried out according to the flow charts illustrated in FIG. 2 and FIG. 5 in the fifth embodiment. Characteristics of a steel sheet used as the work are listed in Table 1. The measurement of strain of the dies is same as described in Example 1. Also the methods of application of the flow chart in FIG. 2 is same as described in Example 1.

In step S203 (extraction from the reference data), out of the reference data stored in the storage unit 104, the reference data, which gives the minimum total of differences between the production conditions of the reference data extracted from the storage unit 104 and the production conditions of the target data for fracture judgment, over the duration from the time when the stamping proceeds by at least 60% of the stroke of stamping from the start time of stamping, up to the time when a reverse operation of a slide of a stamping press, after reaching the bottom dead position of stamping and turning into the reverse operation, proceeds by at least 20% or more of a stroke of stamping from the bottom dead position, read out from the internal memory device in step S201, is extracted as the comparative data. A specific method of calculating the minimum total of the differences in the production conditions is same as described in Example 1.

In step S401 (judgment of abnormal measurement), out of the data extracted in step S203, a strain waveform of the comparative data, and a strain waveform of the target data for fracture judgment are compared, over the duration from the time when the stamping proceeds by at least 60% of the stroke of stamping from the start time of stamping, up to the time when a reverse operation of a slide of a stamping press, after reaching the bottom dead position of stamping and turning into the reverse operation, proceeds by at least 20% or more of a stroke of stamping from the bottom dead position. If, as a consequence, a correlation coefficient of the strain waveform of the comparative data and the strain waveform of the target data for fracture judgment is smaller than 0.6, the process advances to step S402 so as to place a judgment of "abnormal measurement", and excepts it from the fracture judgment. In contrast, the fracture judgment is carried out only when the correlation coefficient of the strain waveform of the comparative data and the strain waveform of the target data for fracture judgment is 0.6 or larger. A method of calculating the correlation coefficient basically conforms to a method of calculating Pearson's product-moment correlation coefficient.

Actually, the stamping, for obtaining the reference data not targeted at the fracture judgment, was carried out 5,000 times, similarly according to the procedures described in the above. Data collected therefrom were stored in the storage unit 104. The storage unit 104 used herein was a hard disk of a computer.

Next, the target stamping for fracture judgment was carried out 100,000 times. The nearest data was extracted similarly according to the procedures described in the above for each of 100,000 times of stamping, the difference in strain with respect to the comparative data was calculated, and whether the maximum value of difference is equal to or larger than a predetermined value (30 [µε]) is judged. Results of calculation are listed in Table 13. It is understood that the crack detection is highly accurate, showing a rate of normal judgment of 1.66%, with a rate of excessive detection of [ppm], and a miss rate of 30 [ppm].

TABLE 13

| | | | Total number of products | Number of normal products | Number of cracked products |
|---|---|---|---|---|---|
| Results of product inspection | | | 99980 | 98320 | 1660 |
| Rate of abnormality (number of cracked products/total number of products) [%] | | | | 1.66% | |
| Judgment criteria 1 | Judgment by strain measuring unit | | 99995 | 98337 | 1658 |
| | Details of abnormal judgment | Normal judgment (results of product inspection coincide with judgment) | | | 1657 |
| | | Excessive detection | | | 1 |
| | | Missing | | | 3 |
| | Rate of normal judgment (number of normally judged products/total number of products) [%] | | | | 1.66% |
| | Rate of excessive detection (number of excessively detected products/total number of products) [ppm] | | | | 10.0 |
| | Miss rate (number of missed products/total number of products) [ppm] | | | | 30.0 |

The object of the present invention may be achieved also by providing a storage medium, which contains a program code of software realizing the functions of the above-described embodiments recorded therein, to a system or to an apparatus. In this case, a computer (or CPU and MPU) of the system or the apparatus reads out the program code stored in the storage medium and executes it.

In this case, the program code per se read out from the storage medium realizes the functions in the above-described embodiments, and the program code per se and the storage medium having the program code stored therein configure the present invention.

Flexible disk, hard disk, optical disk, magneto-optical disk, CD-ROM, CD-R, magnetic tape, non-volatile memory tape, non-volatile memory card, ROM and so forth may be adoptable as the storage medium for providing the program code.

Execution of the program code read out by the computer not only realizes the functions of the above-described embodiments. For example, based on instructions by the program code, a part of, or the entire portion of actual processing may be executed by an OS (basic system or operating system) which runs on the computer, and the functions of the above-described embodiments may be realized by the processing.

Another possible mode may be such that the program code read out from the storage medium is written into a memory on a function expansion board inserted to the computer, or owned by a function expansion unit connected to the computer. In this case, after the program code is written in the memory, a CPU or the like owned by the function expansion board or function expansion unit executes a part of, or the entire portion of actual processing based on instructions of the program code, and thereby the functions of the above-described embodiments are realized by the processing.

INDUSTRIAL APPLICABILITY

By the fracture judgment for metal stamped products applied with the present invention, cracks possibly produced in the process of stamping of various metal materials such as those of iron-base, non-iron-base and stacked products may precisely be judged.

The invention claimed is:

1. A method of judging fracture in a metal stamped product which judges fracture in a metal stamped product formed using a punch and a die,
    using a strain measuring unit which measures strain of at least either of the punch and the die selected as a target die to be measured, and
    a storage unit which stores, as reference data, strain of the target die to be measured over the entire period or a partial period from the start time of stamping to the finishing time of stamping, and production conditions including at least sliding speed, with respect to a plurality of stamped product having no crack produced therein,
    the method comprising:
    an acquisition step which acquires, in a target stamping for fracture judgment, and as target data for fracture judgment, strain of the target die to be measured by the strain measuring unit over the entire period or a partial period from the start time of stamping to the finishing time of stamping, and acquires production conditions including at least sliding speed;
    an extraction step which extracts, from the reference data, the one satisfying a predetermined condition as comparative data, based on the production conditions of the reference data extracted from the storage unit, and also based on the production conditions of the target data for fracture judgment, and
    a judgment step which compares strain in the comparative data and strain in the target data for fracture judgment, and judges occurrence of a crack in a stamped product, if a predetermined condition is satisfied.

2. The method of judging fracture in a metal stamped product according to claim 1, wherein the production conditions further includes, in addition to the sliding speed, at least one of production time, ambient temperature, humidity, blank holding force, lot number of work, blank process position information traceable from material lot, tensile strength of work, yield strength of work, amount of uniform elongation of work, and thickness of work.

3. The method of judging fracture in a metal stamped product according to claim 1, wherein, the extraction step extracts the reference data, which gives the minimum total of differences between the production conditions of the reference data extracted from the storage unit and the production conditions of the target data for fracture judgment, as the comparative data.

4. The method of judging fracture in a metal stamped product according to claim 3, wherein the extraction step extracts the reference data, which gives the minimum total of differences between the production conditions of the reference data extracted from the storage unit and the production conditions of the target data for fracture judgment, over the duration from the start time of stamping up to the time when the stamping proceeds by at least 30% or more of the stroke of stamping, as the comparative data.

5. The method of judging fracture in a metal stamped product according to claim 4, further comprising a step of comparing maximum values of strain of the comparative data over the duration from the start time of stamping up to the time when the stamping proceeds by at least 30% or more of the stroke of stamping, with a maximum value of strain of the target data for fracture judgment; assuming a maximum value of strain of the target data for fracture judgment as a result of blankless stamping if the value is smaller than 20% of a maximum value of strain of the comparative data, and excepting the value from the fracture judgment; and subjecting only a maximum value of strain of the target data for fracture judgment not smaller than 20% of the maximum value of strain of the comparative data, to the judgment step.

6. The method of judging fracture in a metal stamped product according to claim 4, further comprising a step of comparing strain waveforms of the comparative data over the duration from the start time of stamping up to the time when the stamping proceeds by at least 30% or more of the stroke of stamping, with a strain waveform of the target data for fracture judgment; assuming a strain waveform of the target data for fracture judgment as a result of abnormal measurement if the waveform shows a correlation coefficient with respect to the strain waveform of the comparative data of smaller than 0.6, and excepting the strain waveform from the fracture judgment; and subjecting only a strain waveform of the target data for fracture judgment showing a correlation coefficient with respect to the strain waveform of the comparative data of not smaller than 0.6, to the judgment step.

7. The method of judging fracture in a metal stamped product according to claim 3, wherein the extraction step extracts the reference data, which gives the minimum total of differences between the production conditions of the reference data extracted from the storage unit and the production conditions of the target data for fracture judgment, over the duration from the time when the stamping proceeds by at least 60% of the stroke of stamping from the start time of stamping, up to the time when a reverse operation of a slide of a stamping press, after reaching the bottom dead position of stamping and turning into the reverse operation, proceeds by at least 20% or more of the stroke of stamping from the bottom dead position, as the comparative data.

8. The method of judging fracture in a metal stamped product according to claim 7, further comprising a step of comparing strain waveforms of the comparative data over the duration from the time when the stamping proceeds by at least 60% of the stroke of stamping from the start time of stamping, up to the time when a reverse operation of a slide of a stamping press, after reaching the bottom dead position of stamping and turning into the reverse operation, proceeds by at least 20% or more of the stroke of stamping from the bottom dead position, with a strain waveform of the target data for fracture judgment; assuming a strain waveform of the target data for fracture judgment as a result of abnormal measurement if the waveform shows a correlation coefficient with respect to the strain waveform of the comparative data of smaller than 0.6, and excepting the strain waveform from the fracture judgment; and subjecting only a strain waveform of the target data for fracture judgment showing a correlation coefficient with respect to the strain waveform of the comparative data of not smaller than 0.6, to the judgment step, over the duration from the time when the stamping proceeds by at least 60% of the stroke of stamping from the start time of stamping, up to the time when a reverse operation of a slide of a stamping press, after reaching the bottom dead position of stamping and turning into the reverse operation, proceeds by at least 20% or more of a stroke of stamping from the bottom dead position.

9. The method of judging fracture in a metal stamped product according to claim 1, wherein the judgment step judges occurrence of a crack in a stamped product, if a maximum value of difference between strain of the comparative data and strain of the target data for fracture judgment exceeds a predetermined value.

10. The method of judging fracture in a metal stamped product according to claim 1, wherein, further by using a blank holding die, at least one of the punch, the die and the blank holding die is selected as the target die to be measured.

11. The method of judging fracture in a metal stamped product according to claim 1, wherein the extraction step extracts the reference data based on production conditions of the reference data extracted from the storage unit, and production conditions of the target data for fracture judgment, over the duration from the start time of stamping up to the time when the stamping proceeds beyond a predetermined range of the stroke of stamping, as the comparative data.

12. A fracture judgment apparatus for judging fracture in a metal stamped product which judges fracture in a metal stamped product formed using a punch and a die, comprising:

a strain measuring unit which measures strain of at least either of the punch and the die selected as a target die to be measured; and a storage unit which stores, as reference data, strain of the target die to be measured over the entire period or a partial period from the start time of stamping to the finishing time of stamping, and production conditions including at least sliding speed, with respect to a plurality of stamped product having no crack produced therein;

an acquisition unit which acquires, in a target stamping for fracture judgment, and as target data for fracture judgment, strain of the target die to be measured by the strain measuring unit over the entire period or a partial period from the start time of stamping to the finishing time of stamping, and acquires production conditions including at least sliding speed;

an extraction unit which extracts, from the reference data, the one satisfying a predetermined condition as comparative data, based on the production conditions of the reference data extracted from the storage unit, and also based on the production conditions of the target data for fracture judgment; and a judgment unit which compares strain in the comparative data and strain in the target data for fracture judgment, and judges occurrence of a crack in a stamped product, if a predetermined condition is satisfied.

13. A non-transitory computer-readable medium having a program stored thereon, the program having instructions to be executed by a processor, the instructions which, when executed, cause the processor to execute fracture judgment of a metal stamped product, which judges fracture in a metal stamped product formed using a punch and a die, using a strain measuring unit which measures strain of at least either of the punch and the die selected as a target die to be measured, and a storage unit which stores, as reference data, strain of the target die to be measured over the entire period or a partial period from the start time of stamping to the finishing time of stamping, and production conditions including at least sliding speed, with respect to a plurality of stamped product having no crack produced therein, the program comprising:

an acquisition process which acquires, in a target stamping for fracture judgment, and as target data for fracture judgment, strain of the target die to be measured by the strain measuring unit over the entire period or a partial period from the start time of stamping to the finishing time of stamping, and acquires production conditions including at least sliding speed;

an extraction process which extracts, from the reference data, the one satisfying a predetermined condition as comparative data, based on the production conditions of the reference data extracted from the storage unit, and also based on the production conditions of the target data for fracture judgment; and a judgment process which compares strain in the comparative data and strain in the target data for fracture judgment, and judges occurrence of a crack in a stamped product, if a predetermined condition is satisfied.

* * * * *

UNITED STATES PATENT AND TRADEMARK OFFICE
CERTIFICATE OF CORRECTION

PATENT NO. : 8,464,591 B2  Page 1 of 1
APPLICATION NO. : 12/998291
DATED : June 18, 2013
INVENTOR(S) : Takuya Kuwayama et al.

It is certified that error appears in the above-identified patent and that said Letters Patent is hereby corrected as shown below:

In the Specification

Column 21, line 27, change "[pc]" to -- [µε] --

Column 21, line 35, change "[µϵ]" to -- [µε] --

Column 22, line 49, change "[pc]" to -- [µε] --

Column 22, line 62, change "[pc]" to -- [µε] --

Column 24, line 38, change "[µϵ]" to -- [µε] --

Column 26, line 20, change "[µϵ]" to -- [µε] --

Column 28, line 12, change "[µϵ]" to -- [µε] --

Column 29, line 24, change "[µϵ]" to -- [µε] --

Column 31, line 3, change "[µϵ]" to -- [µε] --

Signed and Sealed this
Twenty-fourth Day of December, 2013

Margaret A. Focarino
*Commissioner for Patents of the United States Patent and Trademark Office*

UNITED STATES PATENT AND TRADEMARK OFFICE
CERTIFICATE OF CORRECTION

PATENT NO. : 8,464,591 B2  Page 1 of 1
APPLICATION NO. : 12/998291
DATED : June 18, 2013
INVENTOR(S) : Kuwayama et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 122 days.

Signed and Sealed this
Eighth Day of September, 2015

Michelle K. Lee
*Director of the United States Patent and Trademark Office*